US012702745B2

(12) United States Patent
Smith et al.

(10) Patent No.: US 12,702,745 B2
(45) Date of Patent: Aug. 11, 2026

(54) LEAKAGE CURRENT MANAGEMENT SYSTEMS, DEVICES, AND METHODS

(71) Applicant: NxStage Medical, Inc., Lawrence, MA (US)

(72) Inventors: Mark F. Smith, Waltham, MA (US); Ilya Karnauk, Waltham, MA (US); Eric Zoglio, Derry, NH (US)

(73) Assignee: NxStage Medical, Inc., Lawrence, MA (US)

( * ) Notice: Subject to any disclaimer, the term of this patent is extended or adjusted under 35 U.S.C. 154(b) by 615 days.

(21) Appl. No.: 18/009,091

(22) PCT Filed: Jul. 14, 2021

(86) PCT No.: PCT/US2021/041617
§ 371 (c)(1),
(2) Date: Dec. 8, 2022

(87) PCT Pub. No.: WO2022/015846
PCT Pub. Date: Jan. 20, 2022

(65) Prior Publication Data

US 2023/0277744 A1 Sep. 7, 2023

Related U.S. Application Data

(60) Provisional application No. 63/195,495, filed on Jun. 1, 2021, provisional application No. 63/052,978, filed on Jul. 17, 2020.

(51) Int. Cl.
*A61M 1/36* (2006.01)
*A61B 5/00* (2006.01)
(Continued)

(52) U.S. Cl.
CPC .......... *A61M 1/367* (2013.01); *A61M 1/3639* (2013.01); *A61M 1/3653* (2013.01);
(Continued)

(58) Field of Classification Search
CPC .......... A61M 1/367; A61M 2205/3317; A61M 1/14; A61M 1/3621; A61M 39/28;
(Continued)

(56) References Cited

U.S. PATENT DOCUMENTS

| | | | |
|---|---|---|---|
| 2,709,785 | A | 5/1955 | Ernest |
| 3,015,061 | A | 12/1961 | Jan |

(Continued)

FOREIGN PATENT DOCUMENTS

| | | | |
|---|---|---|---|
| CN | 103328960 | A | 9/2013 |
| WO | 0225277 | A1 | 3/2002 |

(Continued)

OTHER PUBLICATIONS

Extended European Search Report mailed Apr. 17, 2024 for European Patent Application No. 21841250.0.

(Continued)

*Primary Examiner* — Eman A Alkafawi
*Assistant Examiner* — Hugo Navarro
(74) *Attorney, Agent, or Firm* — Potomac Law Group, PLLC

(57) ABSTRACT

A system and a method for reducing leakage current from a patient fluidly connected to a medical device by tubing filled with a conductive fluid, such as blood or dialysate, includes clamping a first current sensor onto the tubing, clamping a transducer that can induce a current in the tubing onto the tubing, and driving the transducer with an appropriate driving signal. The first current sensor detects the magnitude and phase of electrical current in the tubing, while the transducer is driven with a signal that induces an appropriate current in the tubing. The voltage in the tubing resulting from the induced current is at a level that causes the overall voltage drop from the patient to the medical device to be low enough (Continued)

that any leakage current due to this voltage drop is below an acceptable threshold for leakage current.

16 Claims, 31 Drawing Sheets

(51) Int. Cl.

| | |
|---|---|
| ***A61M 1/14*** | (2006.01) |
| ***A61M 1/16*** | (2006.01) |
| ***A61M 1/18*** | (2006.01) |
| ***A61M 1/20*** | (2006.01) |
| ***A61M 1/30*** | (2006.01) |
| ***A61M 5/36*** | (2006.01) |
| ***G01R 31/52*** | (2020.01) |

(52) U.S. Cl.
CPC . *A61M 2205/05* (2013.01); *A61M 2205/3317* (2013.01); *G01R 31/52* (2020.01)

(58) Field of Classification Search
CPC ........ A61M 39/281; A61M 1/36; A61M 1/30; A61M 5/36; A61M 1/3639; A61M 1/3653; A61M 2205/05; G01R 31/52; A61B 5/6866
USPC .......................................................... 324/500
See application file for complete search history.

(56) References Cited

U.S. PATENT DOCUMENTS

| | | | | |
|---|---|---|---|---|
| 3,396,331 | A | 8/1968 | Sperry | |
| 3,867,688 | A | 2/1975 | Koski | |
| 4,155,852 | A * | 5/1979 | Fischel | A61M 1/1664 210/186 |
| 4,540,942 | A | 9/1985 | Yamamura et al. | |
| 4,579,137 | A | 4/1986 | Brandt, Jr. | |
| 5,089,781 | A | 2/1992 | Arichika et al. | |
| 5,268,642 | A | 12/1993 | Uchidomi | |
| 5,631,552 | A | 5/1997 | Ogawa et al. | |
| 5,935,077 | A | 8/1999 | Ogle | |
| 5,959,455 | A | 9/1999 | Brown | |
| 6,626,048 | B1 | 9/2003 | Dam Es et al. | |
| 6,663,585 | B1 * | 12/2003 | Ender | A61M 1/367 210/645 |
| 7,323,964 | B1 | 1/2008 | Shyu et al. | |
| 10,912,877 | B2 | 2/2021 | Fabig et al. | |
| 2007/0018659 | A1 | 1/2007 | Homan et al. | |
| 2008/0065006 | A1 * | 3/2008 | Roger | G01N 27/10 604/65 |
| 2008/0101099 | A1 | 5/2008 | Jacobs | |
| 2008/0128134 | A1 | 6/2008 | Mudunuri et al. | |
| 2010/0185132 | A1 | 7/2010 | Han et al. | |
| 2012/0223795 | A1 | 9/2012 | Hester | |
| 2013/0099808 | A1 | 4/2013 | Li et al. | |
| 2013/0342268 | A1 * | 12/2013 | Samuelsson | A61B 5/0215 327/552 |
| 2014/0031736 | A1 | 1/2014 | Wright et al. | |
| 2015/0348701 | A1 | 12/2015 | Rezanezhad Gatabi | |
| 2016/0334352 | A1 | 11/2016 | Fougere | |
| 2018/0074105 | A1 | 3/2018 | Horanoff et al. | |
| 2018/0296746 | A1 | 10/2018 | Merwe et al. | |
| 2019/0082975 | A1 | 3/2019 | Sano et al. | |
| 2020/0030517 | A1 * | 1/2020 | Basati | A61M 1/159 |
| 2021/0293895 | A1 | 9/2021 | Essawy et al. | |
| 2022/0163484 | A1 | 5/2022 | Yamada et al. | |

FOREIGN PATENT DOCUMENTS

| | | | |
|---|---|---|---|
| WO | 03086504 | A2 | 10/2003 |
| WO | 2017064248 | A1 | 4/2017 |
| WO | 2020007666 | A1 | 1/2020 |
| WO | 2022139991 | A1 | 6/2022 |

OTHER PUBLICATIONS

U.S. Appl. No. 63/129,370, filed Dec. 22, 2020, Mark F. Smith.
International Search Report and Written Opinion dated Dec. 16, 2021, issued in International Application No. PCT/US2021/041617.
Invitation to Pay Additional Fees mailed Sep. 28, 2021 for International Patent Application No. PCT/US2021/041617.

* cited by examiner

LEAKAGE CURRENT MANAGEMENT SYSTEMS, DEVICES, AND METHODS

CROSS-REFERENCE TO RELATED APPLICATIONS

This application is a U.S. national stage filing under 35 U.S.C. § 371 of International Application No. PCT/US2021/041617 filed Jul. 14, 2021, which claims priority to and the benefit of U.S. Provisional Patent Application No. 63/052,978 filed Jul. 17, 2020 and U.S. Provisional Patent Application No. 63/195,495 filed Jun. 1, 2021 all of which are hereby incorporated by reference in their entireties.

BACKGROUND

The use of electrically powered medical devices or equipment connected to a patient is very common in modern medicine. Along with the benefits these devices are designed to bring to a patient, they also can create a potential hazard of electric shock to the patient. Electric shock can be caused by current (referred to as leakage current) flowing through the patient's heart, for instance, creating ventricular defibrillation, which a medical device may induce in an earthed patient or sink to earth if the patient is in contact with another source of electricity. It is desirable to design medical equipment to reduce leakage current.

SUMMARY

When an alternating current (AC) is flowing in a conductive path, which could be a fluid line filled with conductive fluid, the fluid line may be capacitively coupled to a conductive surface next to or near the fluid line. When the fluid line is part of a medical equipment that is coupled to a patient and the conductive surface is at ground potential, the capacitive coupling of the fluid line could cause leakage current to flow through the patient when the patient is electrified with alternating current.

Some embodiments of the disclosure describe a leakage current canceling method. The leakage current from a patient can be reduced by injecting alternating current into a blood line and thus inducting a voltage drop from the blood line entering the medical equipment under test (DUT). This induced voltage drop is intended to be similar in magnitude to the voltage at the patient relative to the DUT. If the injected alternating current is equal to or slightly less than the leakage current, then the leakage current will be reduced by the amount of the injection current. By adjusting the injected alternating current, the leakage current from the patient can be reduced to acceptable levels.

BRIEF DESCRIPTION OF THE DRAWINGS

Embodiments will hereinafter be described in detail below with reference to the accompanying drawings, wherein like reference numerals represent like elements. The accompanying drawings have not necessarily been drawn to scale. Some of the figures may have been simplified by the omission of selected features for the purpose of more clearly showing other underlying features. Such omissions of elements in some figures are not necessarily indicative of the presence or absence of particular elements in any of the exemplary embodiments, except as may be explicitly disclosed in the corresponding written description.

DETAILED DESCRIPTION

Figure 1A:
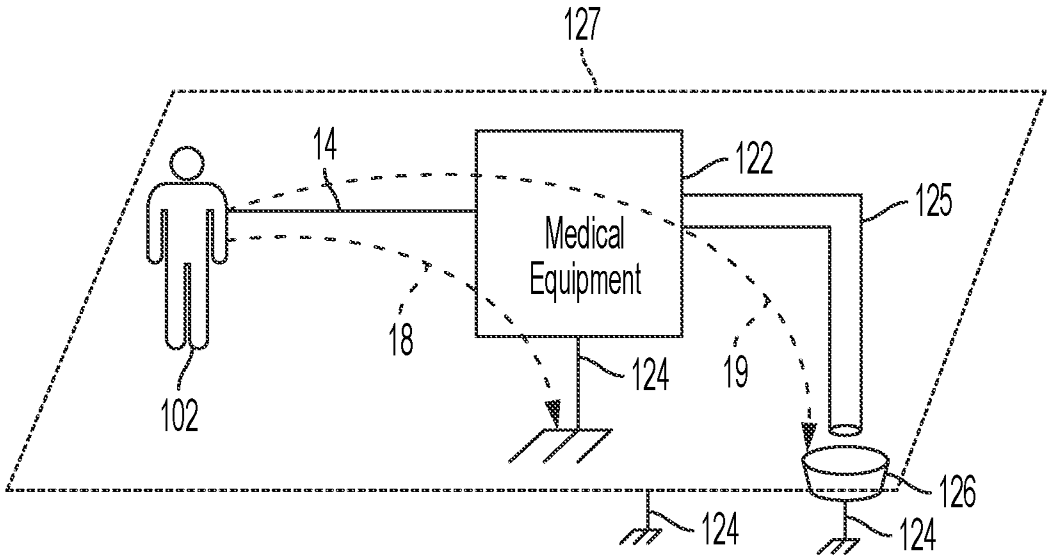
FIG. 1A illustrates an example of a patient connected to medical equipment according to embodiments of the disclosed subject matter.

Referring to FIG. 1A, a patient 102 is undergoing or about to undergo medical treatment by medical equipment 122. In an exemplary embodiment, medical equipment 122 is a blood treatment device, such that patient 102 is connected to the blood treatment device by one or more hollow fluid lines 14 that can convey blood and/or other fluids between the patient 102 and the blood treatment device. Although only a single line is illustrated, it is understood that the illustration represents one or more such lines. In various embodiments, medical equipment 122 may be a hemodialysis treatment device, a hemofiltration treatment device, and any other device that conveys blood and/or other fluids between the patient and the medical equipment 122. In some embodiments, medical equipment 122 is a peritoneal dialysis treatment device that is configured to pump dialysate into the patient's peritoneal cavity and to withdraw spent dialysate from the patient's peritoneal cavity and certain times and/or intervals.

It can be appreciated that the fluid line 14, when filled with a conductive fluid such as blood or dialysate, creates a conductive connection between the patient 102 and the medical equipment 122. This conductive connection creates a possibility of a leakage current 18 and/or 19 to flow between the patient 102 and ground 124, as shown in FIG. 1A. Leakage current 18 could flow from the patient 102 through the medical equipment 122 and to ground 124 via a ground connection between the medical equipment 122 and the ground 124, such as a ground connection as part of an electrical power connection. Alternatively, or additionally, leakage current 19 could flow from the patient to the medical equipment 122 and to ground 124 through another fluid connection of the medical equipment 122, such as a drain line 125. In some embodiments, the medical equipment 122 generates waste (e.g., spent dialysate fluid) that is discarded into a drain 126. The drain 126 may be itself at ground potential. For example, some drain plumbing is made of copper, which is highly conductive and is eventually in physical contact with earth ground. Thus, when a conductive fluid flows through drain line 125, there is a possibility of forming a conductive connection to ground 124 through drain 126. In some embodiments, drain line 125 is a hollow tube formed from an insulating material (e.g., PVC, rubber, plastic, etc.) and the floor 127 of the medical facility where the medical equipment 122 is used is made of metal or other conductive material. In this situation, the conductive fluid in drain line 125 could become capacitively coupled to the floor 127, which is at ground potential, thus creating yet another conductive path for leakage current 19.

Figure 1B:
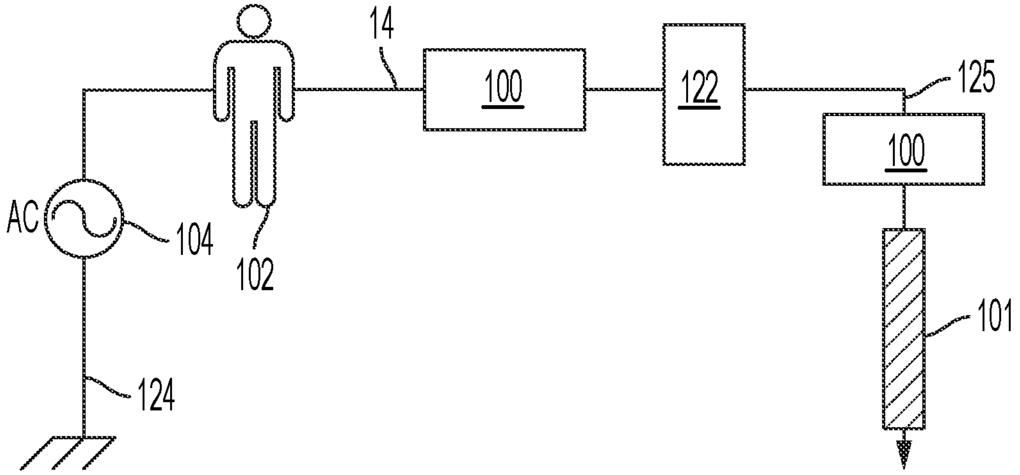
FIG. 1B illustrates systems for reducing leakage current according to embodiments of the disclosed subject matter.

Referring to FIG. 1B, a schematic representation of various embodiments to reduce leakage current 18 and/or 19 is shown. Medical device 122 is electrically coupled to the patient 102 by a conductive path (e.g., through fluid line(s) 14 filled with conductive fluid). The patient 102 may be considered, for testing purposes, to be connected to an AC power source 104, which energizes the patient to a certain voltage. This voltage may be as high as the line voltage (e.g., 120 VAC in the US; 240 VAC in other countries). In a testing environment, when an electrically coupled patient was electrified, leakage current flowing from the patient to the medical device under test ("DUT") was observed. In the testing environment, the conductive path was an electrically conductive fluid flowing in a tube (e.g., a blood line). The patient was electrified with AC during testing, and thus most of the leakage current was capacitive coupled to earth ground either in the DUT itself or capacitively coupled through a drain line from the DUT to a conductive floor. A number of techniques were developed to mitigate this observation, including the embodiments of this disclosure.

To reduce or eliminate the leakage current, a system 100 can be installed on the blood line 14 and/or on the drain line 125, as shown. Further, a shielded drain line 101 can be used instead or in addition to conventional tubing that forms drain line 125, as shown in FIG. 1D.

Figure 1C:
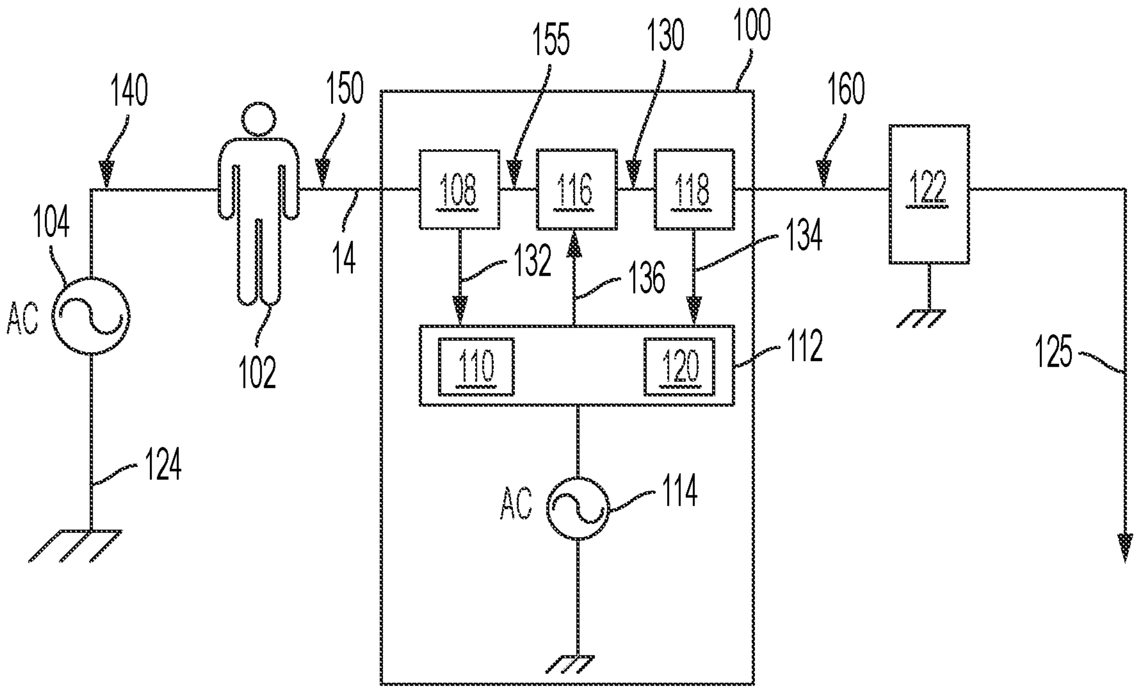
FIGS. 1C and 1F illustrate a system for reducing leakage current according to embodiments of the disclosed subject matter.
Figure 1D:
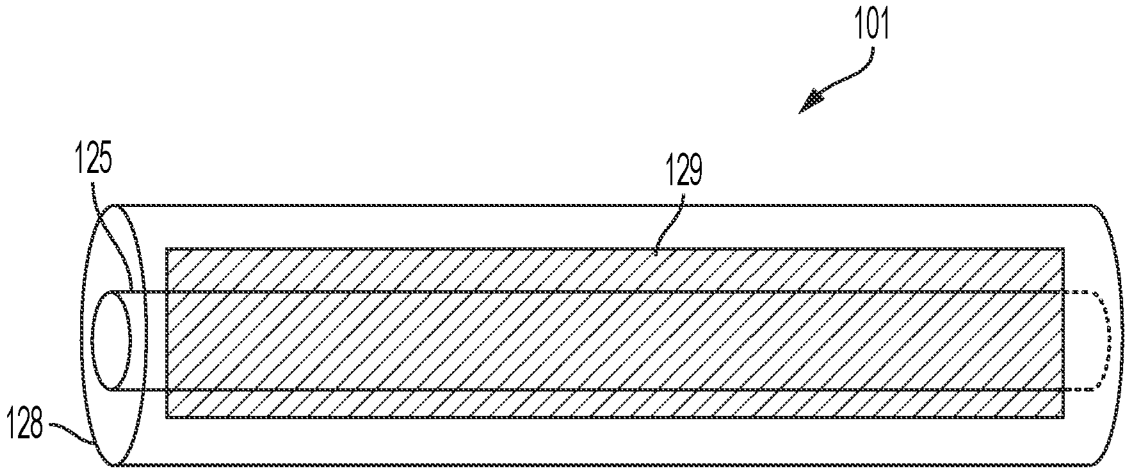
FIG. 1D illustrates a shielded drain line according to embodiments of the disclosed subject matter.

Referring to FIG. 1D, the drain line 125 is surrounded by a conductive shield 129. The conductive shield 129 can be a mesh or a coil of conductive material that surrounds the drain line 125. Other structures that surround the drain line 125 with a conductive material can also be used. Although FIG. 1D illustrates the entirety of the drain line 125 being surrounded by the conductive shield 129, it will be understood that only a portion of the drain line 125 might be so surrounded by conductive shield 129. The conductive shield 129 is further surrounded by an outer tube 128, which is formed of a non-conductive material (such as PVC, rubber, plastic, etc.). In embodiments, the outer tube 128 may be omitted and the conductive shield 129 may be coated with an insulating material, such as latex or other materials.

It has been determined that when drain line 125 is filled with conductive fluid and is in close proximity to another conductor (e.g., metal floor 127), a capacitive coupling may form between the conductive fluid and the conductor. For example, when the drain line is placed on a metal floor that is at ground potential, and the conductive fluid in the drain line 125 is energized with an alternating voltage, a current will flow through the drain line. To mitigate this situation, the voltage in the conductive fluid in drain line 125 is measured (or the current flowing in the conductive fluid) by a sensor (not illustrated in FIG. 1D), and that same voltage is induced on the conductive shield 129 by a driving circuit (not shown). The sensor may be any sensor, such as a contact sensor or a contactless sensor, according to embodiments of the present disclosure. This way, there will be little or no difference in the electrical potential between the conductive fluid in drain line 125 and the conductive shield 129 that surrounds drain line 125. With this arrangement, there is little or no current flow from the conductive fluid in drain line 125, thus reducing any potential leakage current. To the extent that any capacitive coupling is formed, it will be between the conductive shield 129 and the conductive surface, but not from drain line 125 to ground, avoiding leakage current from the patient.

Figure 1E:
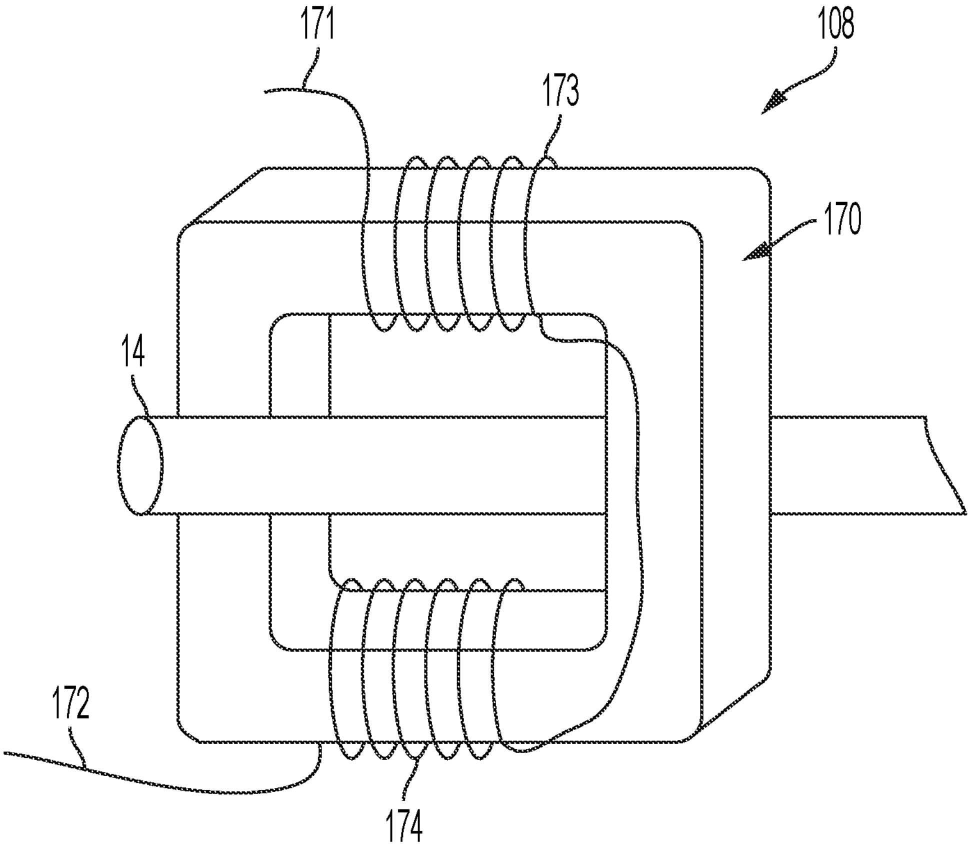
FIG. 1E illustrates a contactless current sensor according to embodiments of the disclosed subject matter.
Figure 1F:
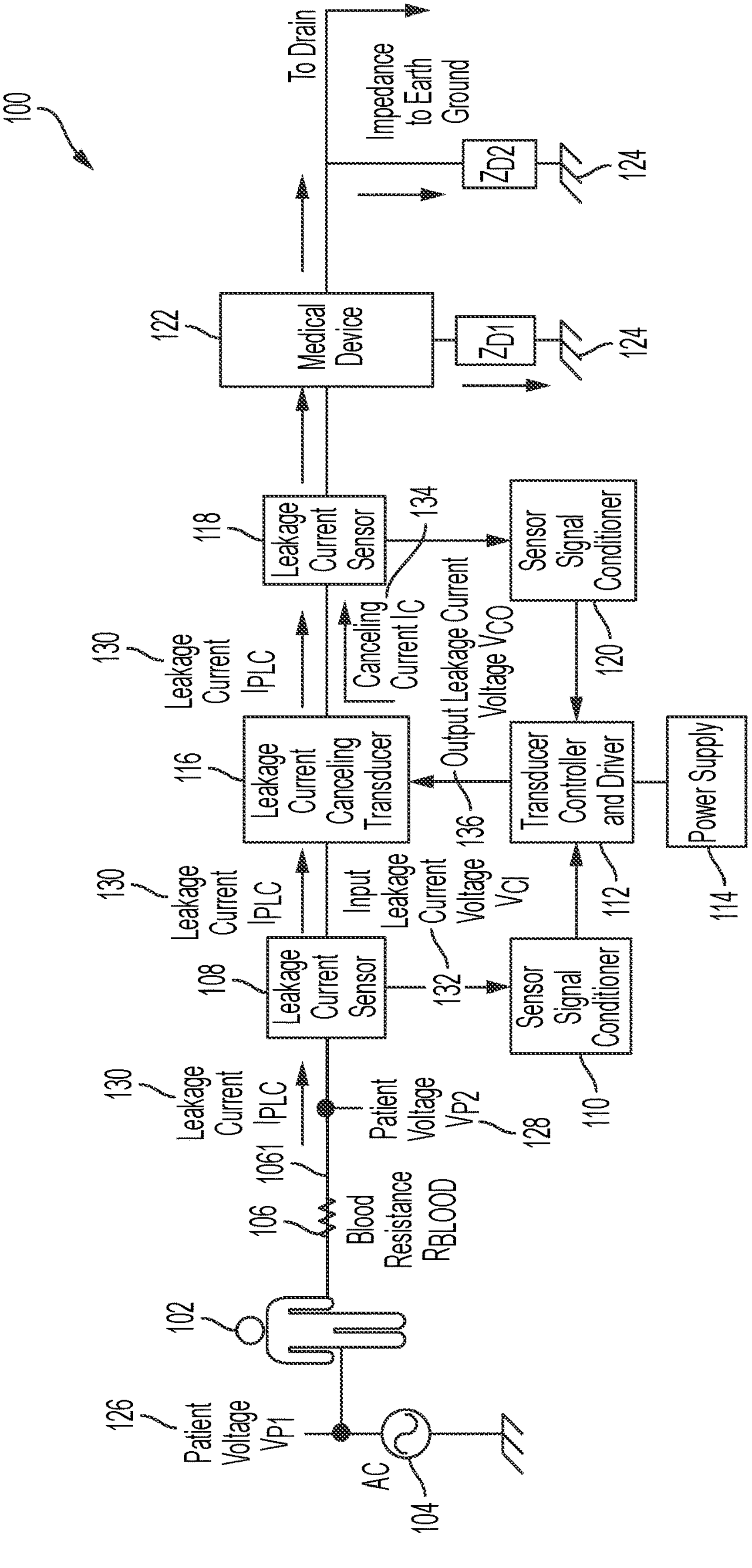

Turning next to FIGS. 1C and 1F, an example of the leakage current cancellation system 100 is described. Embodiments of system 100 reduce current leakage from the patient (e.g., electrified patient) to the medical device by selectively injecting or inducing AC (alternating current) into the conductive fluid (e.g., blood lines) causing a voltage drop from the blood line entering the medical device. The AC is induced by transducer 116. In some embodiments, transducer 116 is contactless, while in other embodiments the transducer 116 may be a contact transducer.

In embodiments, a contact transducer can be one or more electrodes that are electrically coupled to the leakage current reductio system, and are in direct contact with the conductive fluid in which the leakage current flows (e.g., blood, dialysate, waste fluid). As described below, each electrode may take multiple shapes and forms.

In embodiments, one contact electrode is a tube made of a conductive metal, such as stainless steel, silver, gold, titanium, or various metal alloys as described in greater detail below. In further embodiments, the contact electrode is made of a carbon infused polymer and molded or otherwise shaped to interface with one or more fluid lines and electrical connections to the system A contactless transducer does not come into direct contact with the conductive fluid into which current is induced. Instead, the transducer generates a magnetic field, which in turn induces current in the fluid. Exemplary embodiments of such a transducer include a toroid that surrounds the tube 14 and/or 125 conveying conductive fluid. The toroid has wire windings on one or more sides thereof, and when current passes through the wire windings, a magnetic field is generated in the toroid. The magnetic field may be oriented circularly around the tube with conductive fluid, and it may induce an electrical current in the fluid.

A contact transducer is in direct contact with the conductive fluid, so that an electrical current can be injected into the fluid directly from the transducer. In embodiments, the contact transducer includes a conductive tube that is fluidly coupled to the line (14 and/or 125) conveying conductive fluid. The fluid coupling can be achieved via a luer connector, or another similar coupling device. In this configuration, the conductive tube can be conductively connected to, and driven by, a controller to inject a specified current into the conductive fluid passing through the conductive tube.

In an embodiment, the contact electrode is driven with an AC voltage which mirrors the voltage that is detected in the fluid line, but with a phase difference that reduces the detected voltage. The AC voltage can be generated by a control circuit as described below. The control circuit may be implemented as a tracking generator. An example of a tracking generator according to embodiments of the disclosure is described below with reference to FIG. 36.

If the current which is induced in or injected into the conductive fluid is substantially equal to or a threshold less than the leakage current (18, 19), the leakage current will be reduced by the degree of the injected or induced current. Other embodiments can selectively inject or induce any other suitable amount of current to reduce the current leakage from the patient to the medical device.

Referring still to FIG. 1C, patient 102 is illustrated as being connected to AC source 104 to represent a voltage of the patient. The patient 102 is further connected by a fluid line 14 to medical equipment 122. The leakage current reduction system 100 is illustrated as installed on fluid line 14, between the patient 102 and the medical equipment 122. However, system 100 can also be installed on drain line 125 in addition to, or instead of, on the fluid line 14.

In some countries, the standard line voltage is 132 Volts AC, which is the RMS voltage, at 50-60 Hz. The peak-to-peak voltage in this situation is 186 Volts AC.

The system 100 includes a proximal current sensor 108 and a distal current sensor 118, as shown in FIG. 1C. Both of the current sensors detect electrical current flowing through fluid line 14 (i.e., in the conductive fluid that flows through the fluid line 14). System 100 also includes a transducer 116 which is operatively coupled to transducer controller 112. The transducer controller 112 may include signal conditioners 110 and 120, as shown. The signal conditioners may amplify and/or filter the signal output from sensors 108 and 118. The transducer controller 112 is powered by a power supply 114.

Figure 21:
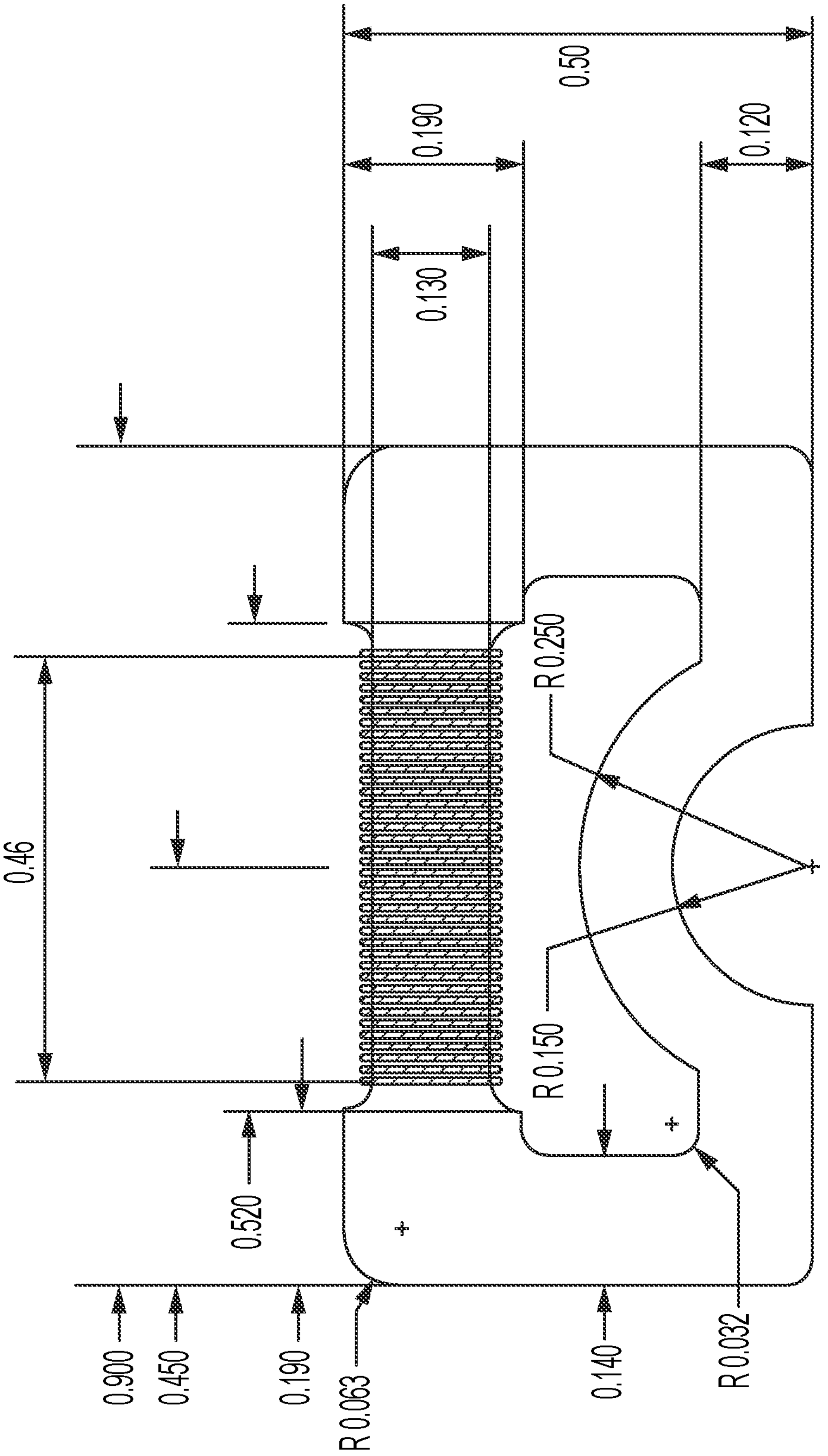
FIG. 21 illustrates a current sensor mechanical design according to embodiments of the disclosed subject matter.

In embodiments, only a single current sensor is used (not shown). In other embodiments, the distal current sensor 118 measures electrical current in fluid line 14. In embodiments, the distal current sensor 118 is a contactless sensor, similar to the transducer 116. For example, sensor 118 may have a generally toroidal shape with one or more wire windings, and be placed around the line 14. In some embodiments, the toroid of sensor 118 may be a single piece, such that line 14 will need to be inserted through the opening in the toroid. In other embodiments, the toroid may have an air gap which allows the toroid to open and close around line 14. A non-limiting example of one half of such an embodiment is illustrated in FIG. 21.

Referring to FIG. 1E, an example of an embodiment of contactless current sensor 108 is described. The sensor has a body 170 which has a toroidal shape, such that an opening in the center is surrounded by a material. The body 170 may be round, square, rectangular, oval, and may have rounded corners. An example of a square with rounded corners is illustrated. The body 170 can be made from a laminated material, such as Carpenter High Permeability 49 alloy ("Carpenter 49") which is a 48% nickel-iron alloy that has high saturation flux density, high magnetic permeability and low core loss.

Fluid line 14 is shown passing through the central opening of the toroidal shape, but it is understood that the sensor can be used on any fluid line (e.g., drain line 125) in addition or instead of fluid line 14. In some embodiments, multiple fluid lines may pass through the central opening at the same time (e.g., a venous blood line and an arterial blood line of a hemodialysis machine). A wire with a first winding 173 and a second winding 174 has ends 171 and 172. The two windings can be connected in series, as shown. In embodiments, the windings may be connected in parallel (not shown). When electrical current, such as alternating current is present in fluid line 14, it generates a magnetic field in the body 170, which in turn induces an electrical current in the wire of the two windings. Thus, a signal representative of the electrical current in the fluid line 14 can be output from ends 171 and 172, and supplied to the controller 112.

In embodiments, the body 170 is split into two halves by an air gap. An example of one half of the body 170 is shown in FIG. 21. It will be understood that the transducer 116 may have a similar or same design as the sensor 108. In embodiments, transducer 116 has four windings connected in series, each on one side of the body 170 (not shown).

In embodiments, the sensor 118 is a contact sensor, such that it is in direct contact with the conductive fluid flowing through line 14. It will be understood that sensor 108 can be the same as sensor 118, but does not need to be. In embodiments, one or both of the sensors 108 and 118 will be a contactless sensor. In embodiments, one or both of the sensors 108 and 118 will be a contact sensor. It will be further understood that contact sensors and contact free sensors can be combined with contact transducers and contactless transducers in all possible combinations.

One benefit of using a contact sensor on a blood line, is that a lower volume of blood needs to be extracted from the patient, as compared with a contactless sensor, especially if multiple windings of a blood line are used to increase the magnetic field.

In embodiments, the distal sensor 118 is used to drive the transducer 116, while the proximal sensor 108 is used as a safety measure to monitor the leakage current from patient 102 and thus verify the operation and status of system 100.

Embodiments of system 100 can reduce the amount of leakage current when a patient is electrified (e.g., by AC mains). For example, a fault condition mitigated by embodiments is when patient 102 is accidentally connected to AC source 104 (e.g., AC mains). An issue can arise when electrical current flows from patient 102 to a low potential, such as earth ground 124. The current can flow from patient 102 to electrically coupled medical device 122 (e.g., a kidney dialysis machine) through a conductive fluid (e.g., blood line 14) and out of medical device 122 to a drain. In this illustrative example, there are multiple current leakage paths to earth ground 124. Some of the leakage paths are in the medical device, another leakage path might be through the drain line to a conductive floor, and yet another leakage path might be the drain line emptying into a copper drain-pipe.

Because of the potential fault and the multiple potential leakage current paths, various current mitigation techniques are disclosed. Embodiments utilize the fluid resistance (e.g., patient blood resistance) to assist in limiting the leakage current. A reduction to the voltage potential drop across the conductive fluid electrical resistance can achieve this objective. Referring back to FIG. 1C, if the patient voltage $V_{P2}$ in line 14 measured at location 150 and the voltage measured at location 160 are nearly the same voltage, then the current through the blood line is nearly zero. This can be achieved by measuring the current (and/or voltage) by sensors 108 and/or 118, and inducing an appropriate current in the line 14 by transducer 116.

Embodiments inject current into the fluid line 14 (e.g., magnetically induce an alternating current via transducer 116) in phase with leakage current $I_{PLC}$ measured in the line 14. The induced current can replace the leakage current into the machine and force $V_{P2}$ to a voltage closer to $V_{P1}$ measured at location 140, thus reducing leakage current $I_{PLC}$ measured at location 155.

Because embodiments of the design have reactive elements, capacitors and inductors, the phasing of the reducing current is non-trivial. Therefore, leakage current $I_{PLC}$ 130 is measured before and after transducer 116 by leakage current sensors 108 and 118. By using the before and after current signals, transducer controller 112 can adjust the phase to be in phase with the $I_{PLC}$ 130 current signal using power supply 114. For example, using the current sensed by leakage current sensors 108 and 118, sensor signal conditioners 110 and 120 can determine input leakage current voltage $V_{CI}$ 132 and output leakage current voltage $V_{CO}$ 136, and provide these voltages to transducer controller 112 such that an induced current $I_c$ 134 can be determined.

In some embodiments, the current sensed by leakage current sensor 108 can be controlled at or near a predefined threshold or range, such as 10 μA or 20 μA via transducer controller 112. The induced current $I_c$ 134 is injected into the fluid stream and summed with the patient leakage current $I_{PLC}$ 130. The resultant current is equal to the current that would have passed through the patient if the canceling transducer were not functional.

An illustrative example is further considered. A patient may be electrified with 132 VAC rms (which is equal to 188 V peak-to-peak). An electrical path can be made from the patient through the patient blood into the medical device and then through the medical device (e.g., dialyzer) to the drain line and eventually to the drain. There are a number of capacitive current leakage paths to earth ground. An informative assumption of a leakage current of 80 μA when the reduction system is not functional presents the following:

Current will flow from the patient to the medical device and then to earth ground to complete the electrical path.

Because of the dimensions of the patient lines, the electrical resistance can be estimated at approximately 103,000 ohms.

With a blood resistance of 103,000 ohms and a leakage current of 80 μA, the voltage drop from the patient to the medical device can be estimated at 8.2 volts. In other word the voltage at the medical device can be estimated at 123.8 VACrms.

The leakage current may split in the machine, with some current flow through the capacitively coupled paths in the machine to earth ground. Other leakage current may flow through capacitively coupled paths from the drain fluid through the walls of tubing to earth ground on the floor.

To mitigate the leakage current issue, embodiments utilize a sensor/transducer (e.g., 108, 116, 118) that is clamped around the blood line. This is an example of a contactless sensor and/or transducer. A magnetic field sensor can be used to sense the current flow in the blood and a canceling transducer can be commanded to inject current into the blood in the same phase as the leakage current from the patient. The canceling transducer can selectively add current to lower the leakage current from the patient to less than 10 μA. For example, the transducer can add at least 75 μA during some implementations. By adding 75 μA, in addition to the 10 μA coming from the patient, the voltage differential from the patient and the medical device will be less than 1.00 VACrms. Accordingly, the transducer injects current into the electrically conductive fluid (e.g., blood line) in phase with the patient leakage current to reduce the voltage differential. To control the transducer coil in phase with the patient leakage current, two sensors are used, the inlet current sensor and the outlet current sensor. For example, the inlet sensor output voltage can be the reference phase signal.

Embodiments of the magnetic current sensor work based on Faraday's law of Induction:

$$V = N\frac{d\emptyset}{dt}$$

This equation indicates that the output voltage of a coil is proportional to the number of turns of wire times the time varying magnetic flux. This equation can be reduced further as follows:

$$V = AN\frac{dB}{dt}$$

This equation breaks down the magnetic flux Ø as the area A times B or A*B. Therefore, we can deduce that the voltage of coil is then proportional to the time varying B field and the area it flows through.

In order to solve leakage current from an electrified patient, embodiments inject a current into a conductive fluid line from the patient (e.g., blood lines) to satisfy the leakage current demand. Embodiments are implemented as a clamp on device so as to not impact the implemented medical device and the disposable.

Embodiments include a novel sensor/transducer pair where, through time periodic magnetic methods, a current can be injected into an electrically conductive fluid. The injected current is configured to be in-phase with the current in the fluid. It was understood that the frequency of the leakage current will be from 45 Hz to 65 Hz. Embodiments also utilize an open design to allow for the patient lines (e.g., PVC tubing) to be placed into the sensor/transducer pair and then closed. Embodiments include several cost efficient and flexible design considerations such that the current leakage reduction system can be readily implemented.

The sensor function is similar to a current transformer. For example, the primary of the transformer is the fluid line and secondary is a winding on the leakage current sensor. A unique core design was created so the sensor could be opened and a fluid tube could be placed in the sensor. When the sensor is closed the sensor completes the magnet circuit and functions as a current sensor.

When the magnetic current sensor is clamped around a tube with electrically conductive fluid and a time periodic current flows in the electrically conductive fluid, a B field is generated and couples into the magnetic circuit. A coil is wound around the sensor core and senses the time varying B field and thus induces a voltage on the coil through Faraday's law of induction. Therefore, the sensor produces a voltage proportional to the current flowing in the fluid.

Figure 2:
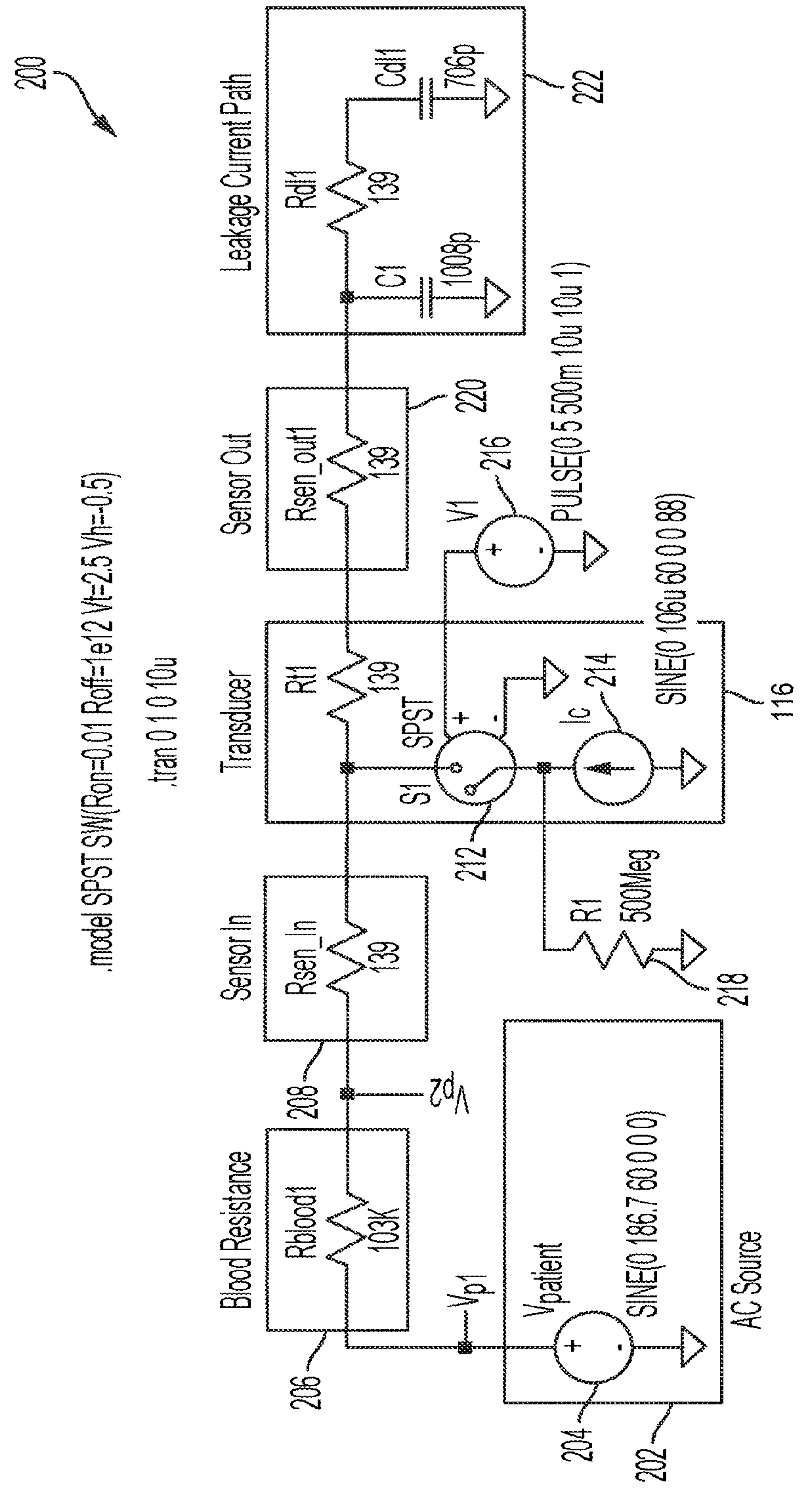
FIG. 2 illustrates an example model of the leakage current reduction system according to embodiments of the disclosed subject matter.

FIG. 2 illustrates a non-limiting example model of the leakage current reduction system according to embodiments of the disclosed subject matter. Although FIG. 2 includes component values, these are merely illustrative and not limiting. FIG. 2 represents a simulation of an electrified patient that generates current leakage reduced by embodiments of this disclosure. Model 200 uses AC source 202 to emulate the patient being electrified with 132 VAC rms at 60 Hz. $V_{P1}$ is the patient voltage. The electrical resistance of the blood is represented by Rblood1 206 and is 103K ohms (as determined by calculation of 2 meters of patient line). Next is $V_{P2}$ which represents the voltage at the medical device, or at the end of the blood line at the medical device. The inlet magnetic current sensor is represented by Rsen_in 208. The resistance of Rsen_in 208 was calculated and determined to be approximately 139 ohms. When using a simulator such as LTSPICE, the current through Rsen_in is a simple measurement of current through a resistor.

Transducer 116 includes an electrical model with a current source 214, such as a sine wave current source running at 75μArms and 60 Hz. Current source 214 for transducer 116 has a phase shift from the patient voltage source $V_{patient}$, such as a phase shift by 88 degrees. Voltage controlled switch 212 was included in the electrical model to aid in detecting/measuring when the reduction current was applied to the fluid. In addition, Rt1 was included, similar to the current sensor. Rt1 has a sample resistance of 139 ohms based upon calculations. V1 216 and R1 218 are also included for simulation purposes.

A second sensor, Rsen_out 220 is used to aid the phasing determination for current source 214. The current through Rsen_out 220 is approximately what the leakage current would be if no canceling was performed. Lastly, a resistor and capacitor network are used to represent the leakage current path 222 to earth ground. C1 represents the leakage path to ground in the medical device and Rdl1 and Cdl1 represent the leakage current through the drain line. Model 200 is setup to have 85 μA rms leakage current when switch 212 is turned off and approximately 10 μA rms when switch 212 is turned on and transducer 210 is functional. A number of elements of model 200 were merely present for simulation and are optional or entirely unnecessary for implementation.

Figure 3:
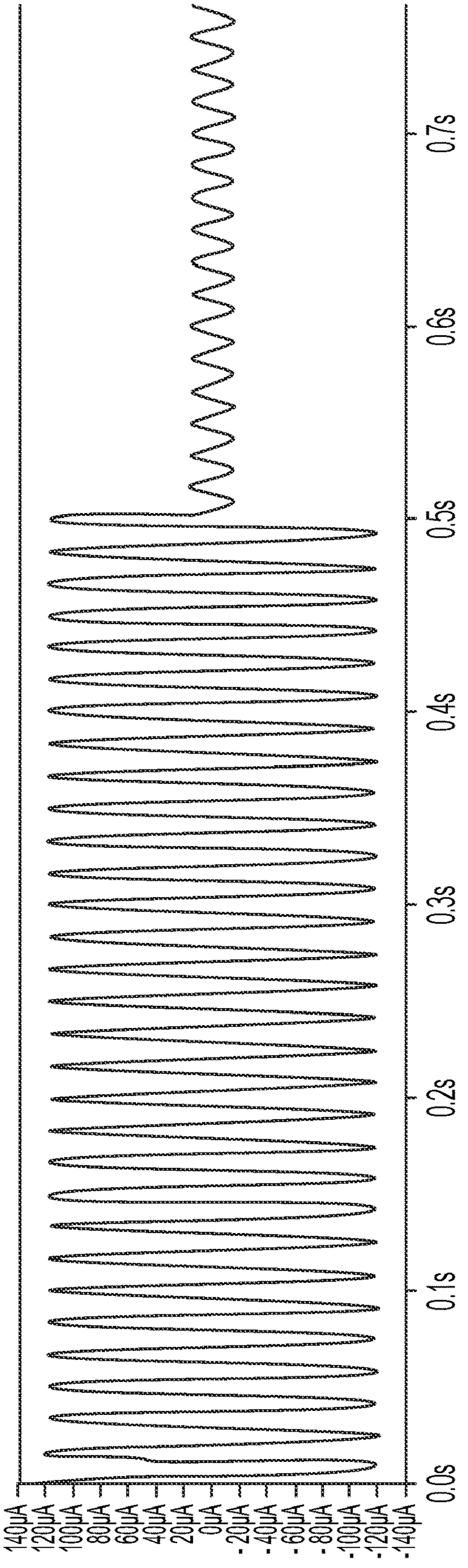
FIG. 3 illustrates leakage current sensed at an input sensor in an example simulation according to embodiments of the disclosed subject matter.
Figure 4:
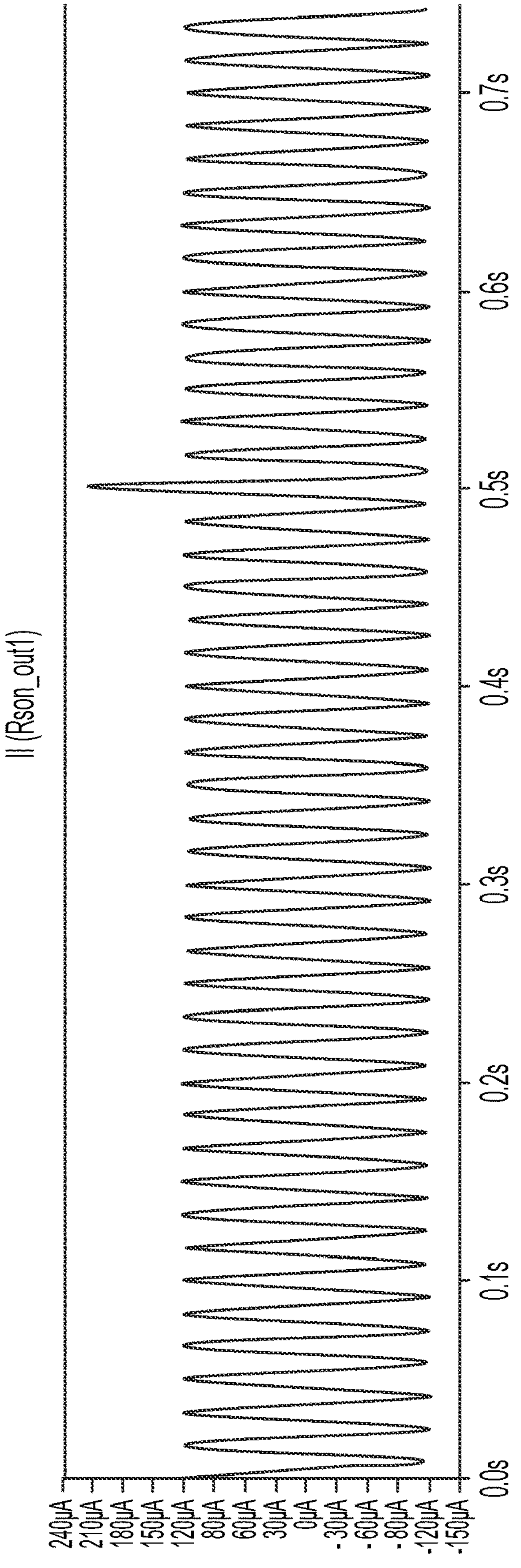
FIG. 4 illustrates leakage current sensed at an output sensor in an example simulation according to embodiments of the disclosed subject matter.
Figure 5:
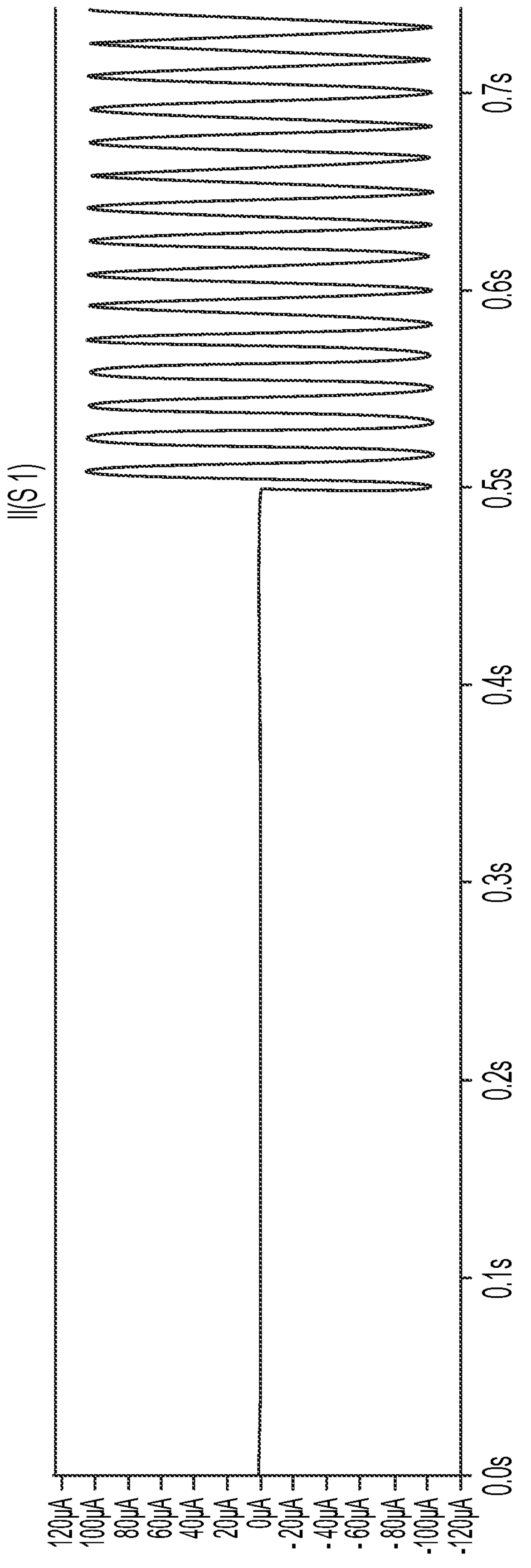
FIG. 5 illustrates current supplied by a current source in an example simulation according to embodiments of the disclosed subject matter.

Measured and injected current from an example simulation are illustrated in FIGS. 3-5. FIG. 3 shows the leakage current sensed at Rsen_in 208 in the example simulation. FIG. 4 shows the leakage current sensed at Rsen_out 220 in the example simulation. FIG. 5 shows the current supplied by current source 214 in the example simulation.

Figure 6:
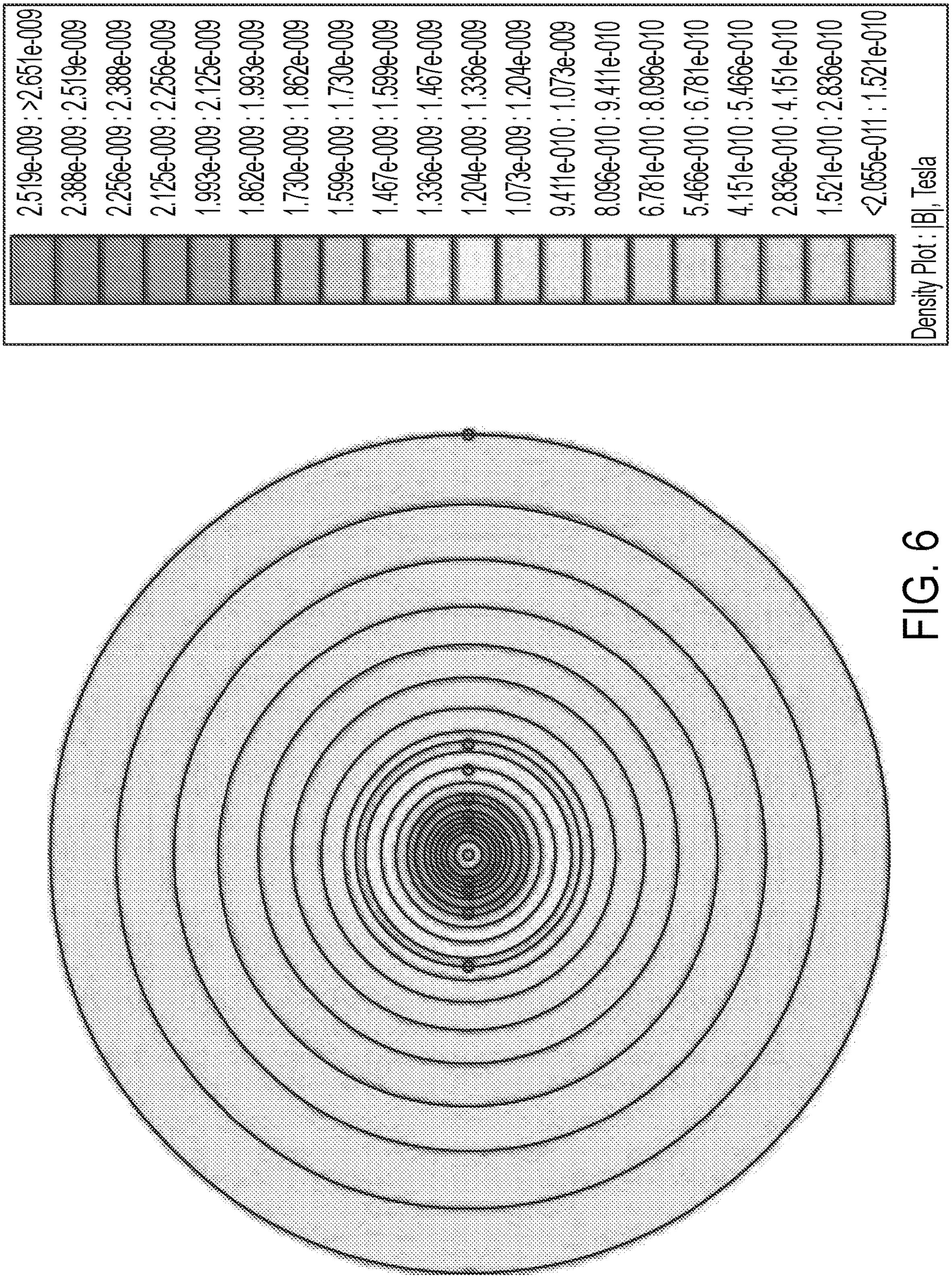
FIGS. 6-8 illustrate graphical depictions of magnetic fields according to embodiments of the disclosed subject matter.
Figure 7:
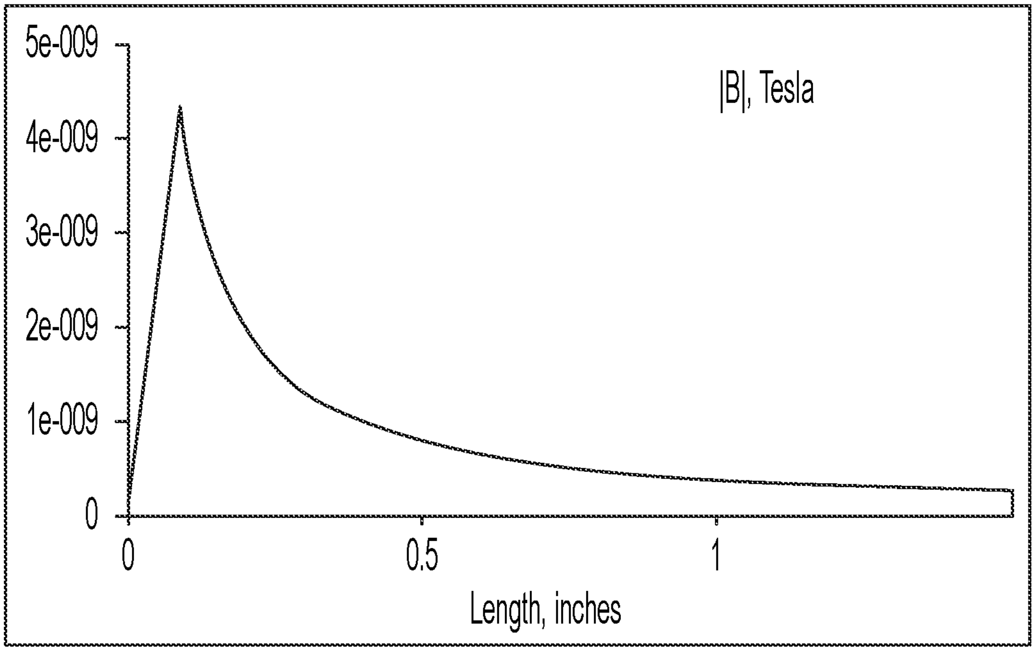
Figure 8:
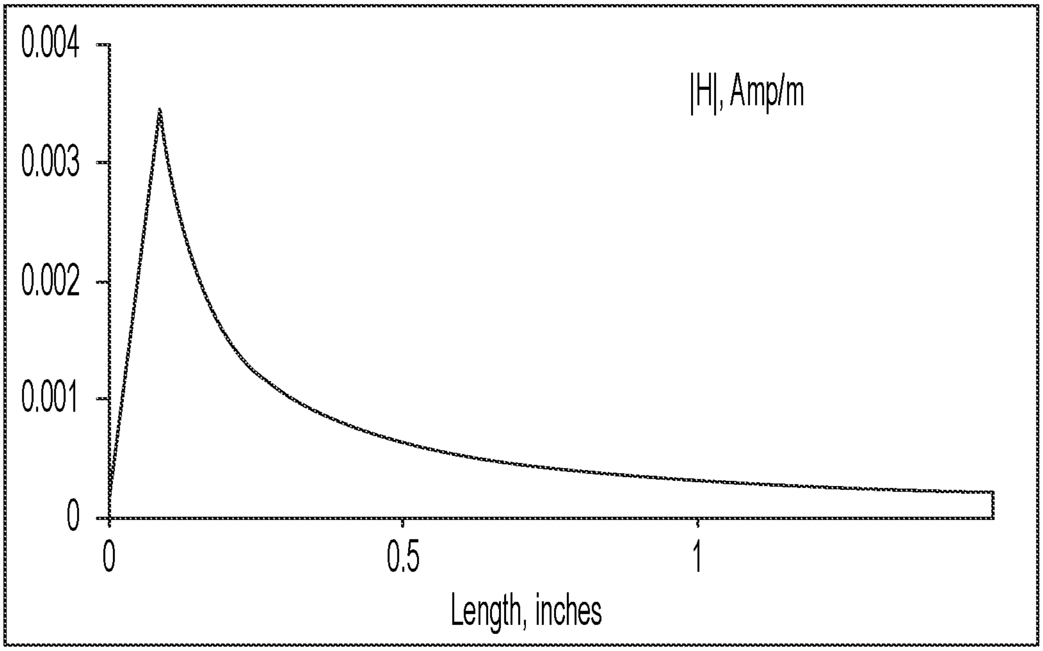

FIGS. 6-8 illustrate graphical depictions of magnetic field measurements based on some embodiments. FIG. 6 illustrates current in a tube B magnetic field (density plot: Tesla). FIG. 7 illustrates the B magnetic field measured in Tesla in the air plotted against distance (in inches). FIG. 8 illustrates the H magnetic field measured in amps/meter in the air plotted against distance.

Figure 9:
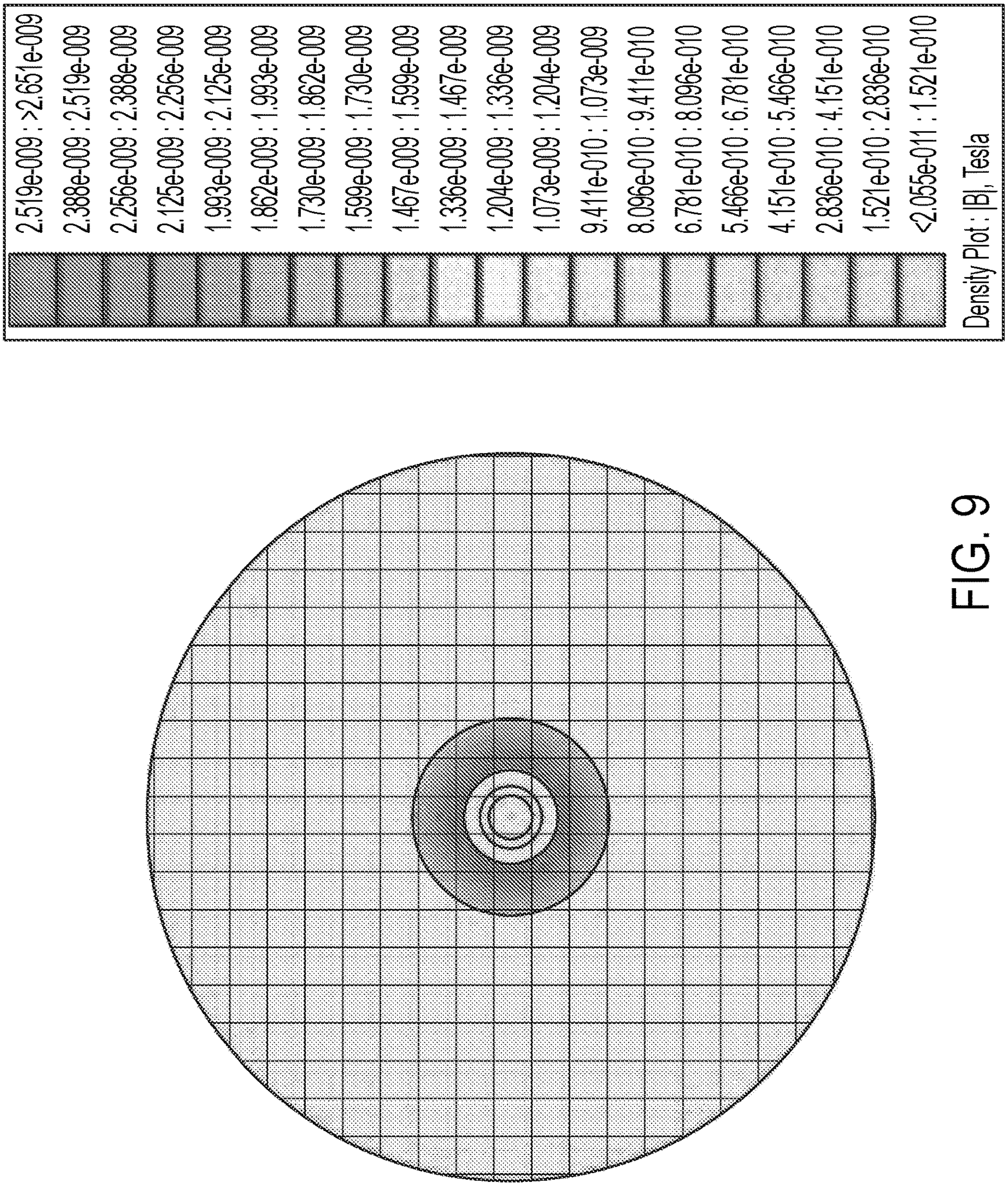
FIGS. 9-11 illustrate graphical depictions of magnetic fields based on a ferrite toroid structure according to embodiments of the disclosed subject matter.
Figure 10:
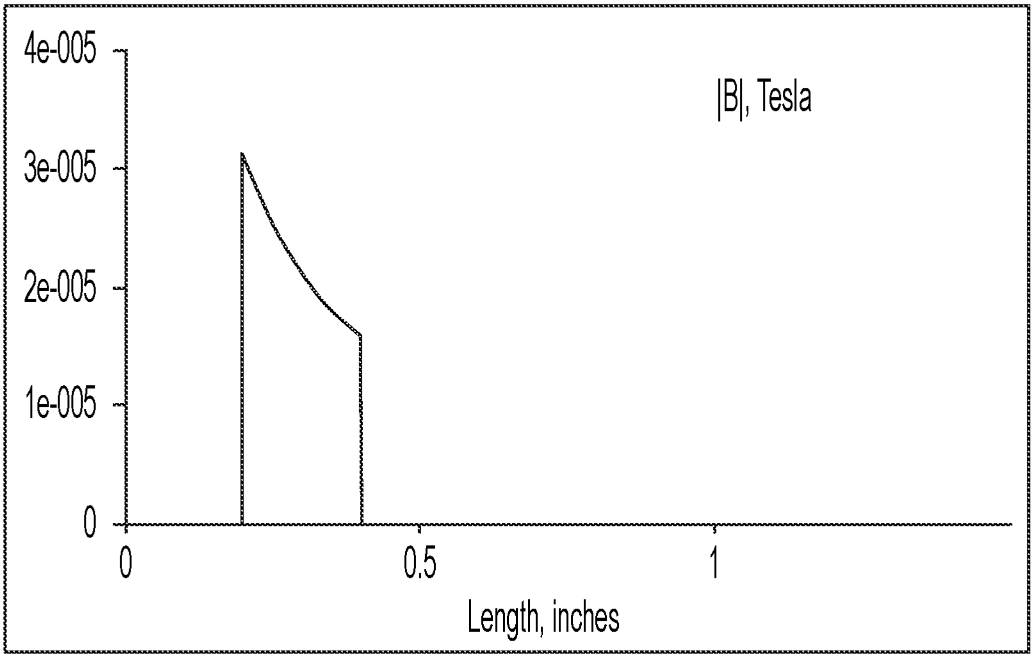
Figure 11:
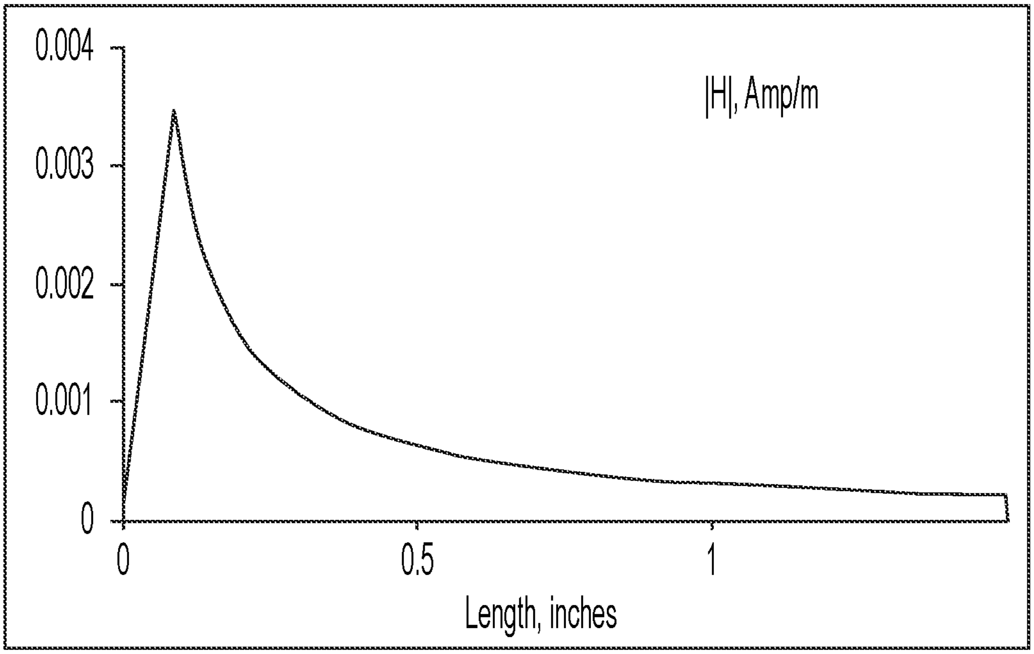

FIGS. 9-11 illustrate graphical depictions of magnetic field measurements based on ferrite toroid structural embodiments. FIG. 9 illustrates current in a tube B magnetic field (density plot: Tesla) using a ferrite toroid. FIG. 10 illustrates the B field measured in Tesla for a ferrite toroid around a tube plotted against distance (in inches). FIG. 11 illustrates the H field measured in amps/meter for a ferrite toroid around a tube plotted against distance.

Embodiments of the leakage current sensor measure the alternating current flowing in the conductive fluid (e.g., blood line), or the leakage current. In some implementations, the sensor can be a non-blood contact sensor that measures the current in a tube. In some implementations, the sensor also includes an open space for conductive fluid tubing to be inserted.

Figure 12:
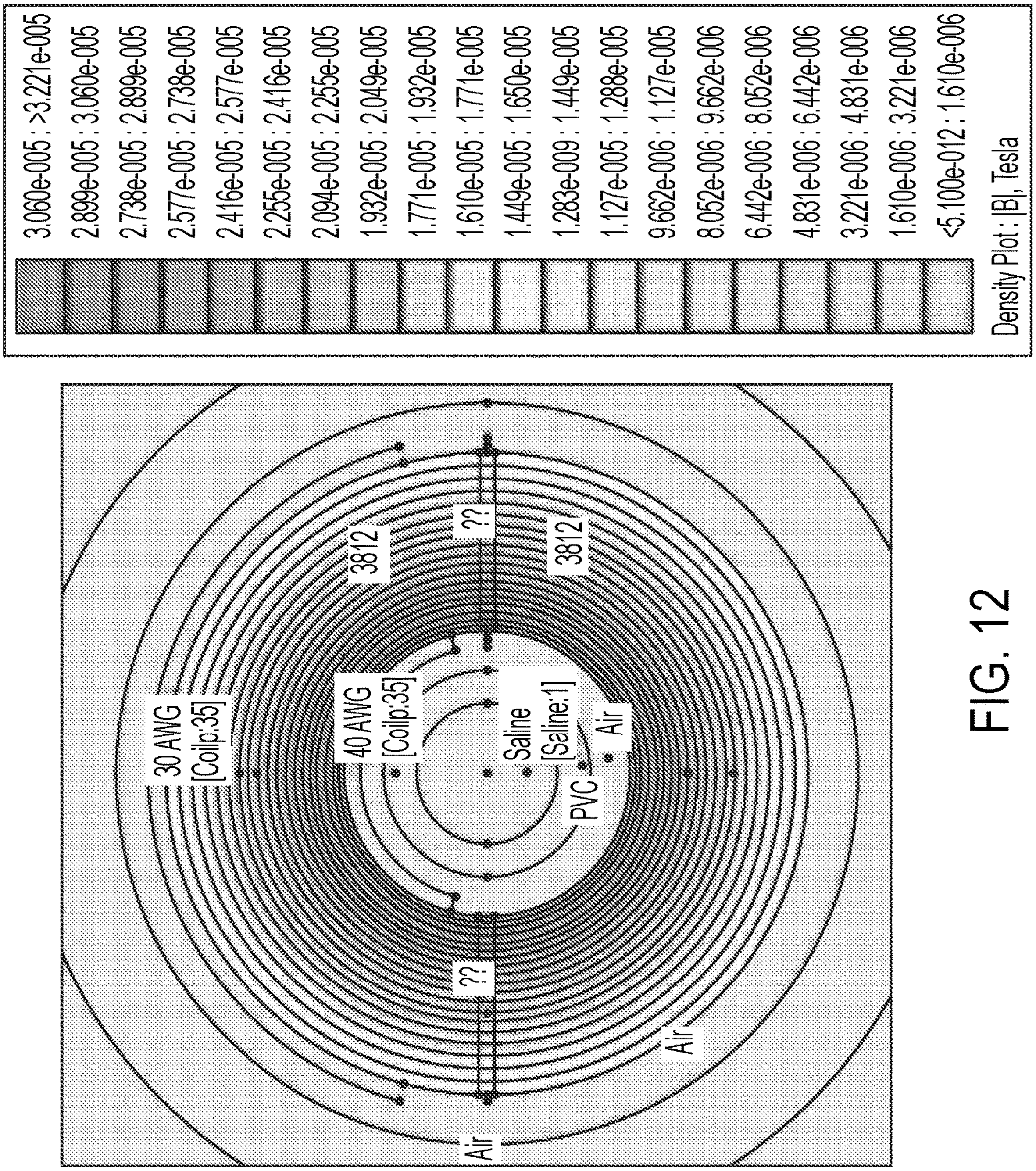
FIG. 12 illustrates a cross-section view of a solid toroid and a graphical depiction of a magnetic field according to embodiments of the disclosed subject matter.

Embodiments include a time periodic magnetic sensor. For example, the magnetic sensor can include structural similarities with a transformer. One embodiment utilizes a solid toroid that includes a winding wrapped around the toroid. FIG. 12 a cross-section view of the solid toroid and a graphical depiction of a magnetic field according to embodiments of the disclosed subject matter. The following results were observed:

Air gap: 0.0000" (no air gap)
Fluid Current: 50 μA
Coil Voltage: 12.55 uVrms
Primary Inductance: 19.03 uH
Required amplification (calculated): 32430 (0.0324e6)

Figure 13:
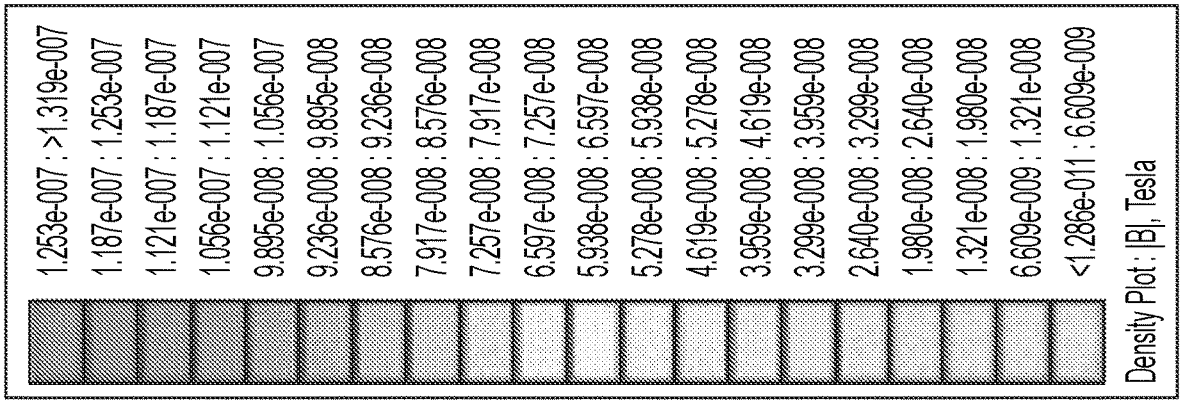
FIGS. 13 and 14 illustrate cross-section views of a split toroid with an air gap and graphical depictions of magnetic fields according to embodiments of the disclosed subject matter.
Figure 13:
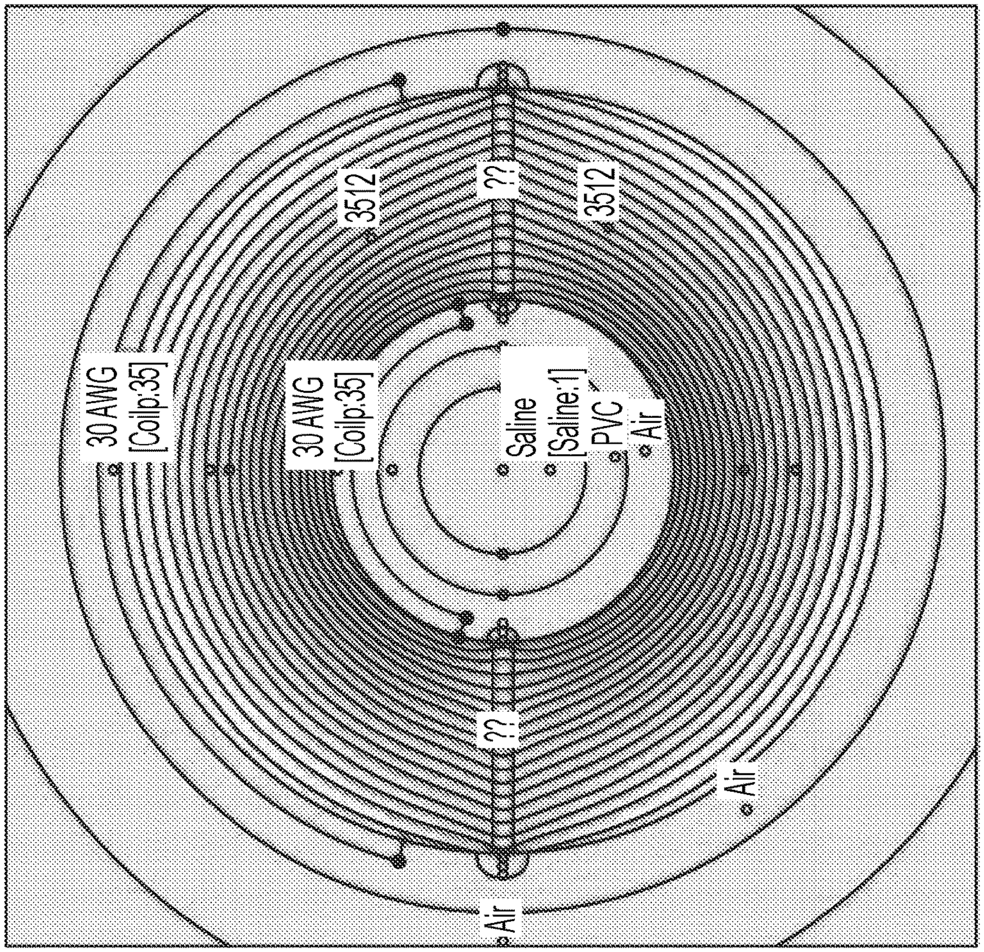
Figure 14:
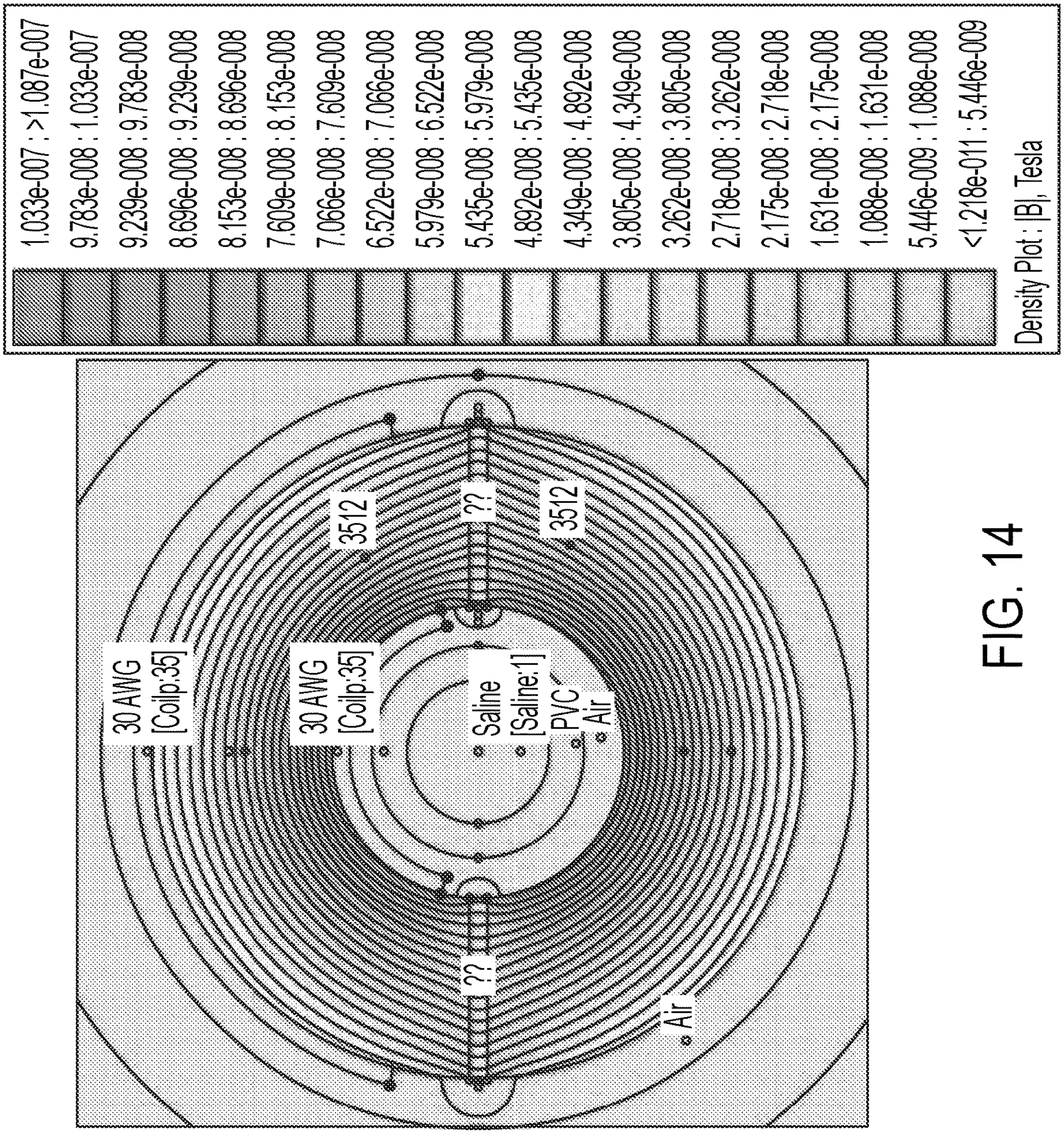

In another embodiments, a ferrite toroidal core that was split in half using a diamond slitting saw. In this embodiment, one half of the toroidal core was wrapped with magnet wire. FIGS. 13 and 14 illustrate cross-section views of a split toroid with an air gap and graphical depictions of magnetic fields according to embodiments of the disclosed subject matter. The following results were observed for the split toroid of FIG. 13:

Air Gap: 0.016"
Fluid Current: 50 μA
Coil Voltage: 51.48 nV
Primary Inductance: 79.8 nH
Required amplification: 9710000 (9.71e6)

The following results were observed for the split toroid of FIG. 14:

Air Gap 0.020"
Fluid Current: 50 μA
Coil Voltage: 42.30 nV

Primary Inductance: 65.9 nH

Vibration sensitivity analysis was performed to determine how sensitive the sensor was to vibration due to the air gap produced by the split core. Minor disturbances, such as tapping on the table where the sensor resides, would cause perturbations to the electrical signal. One concept to make a split core sensor design less sensitive to vibration is to make two circular magnetic paths, one on the top and one on the bottom. A split toroidal design has two half circles which forces the magnetic path through the air gap. The new concept creates two independent magnetic circuits which in theory would reduce the vibration effect caused by vibration noise.

Figure 15:
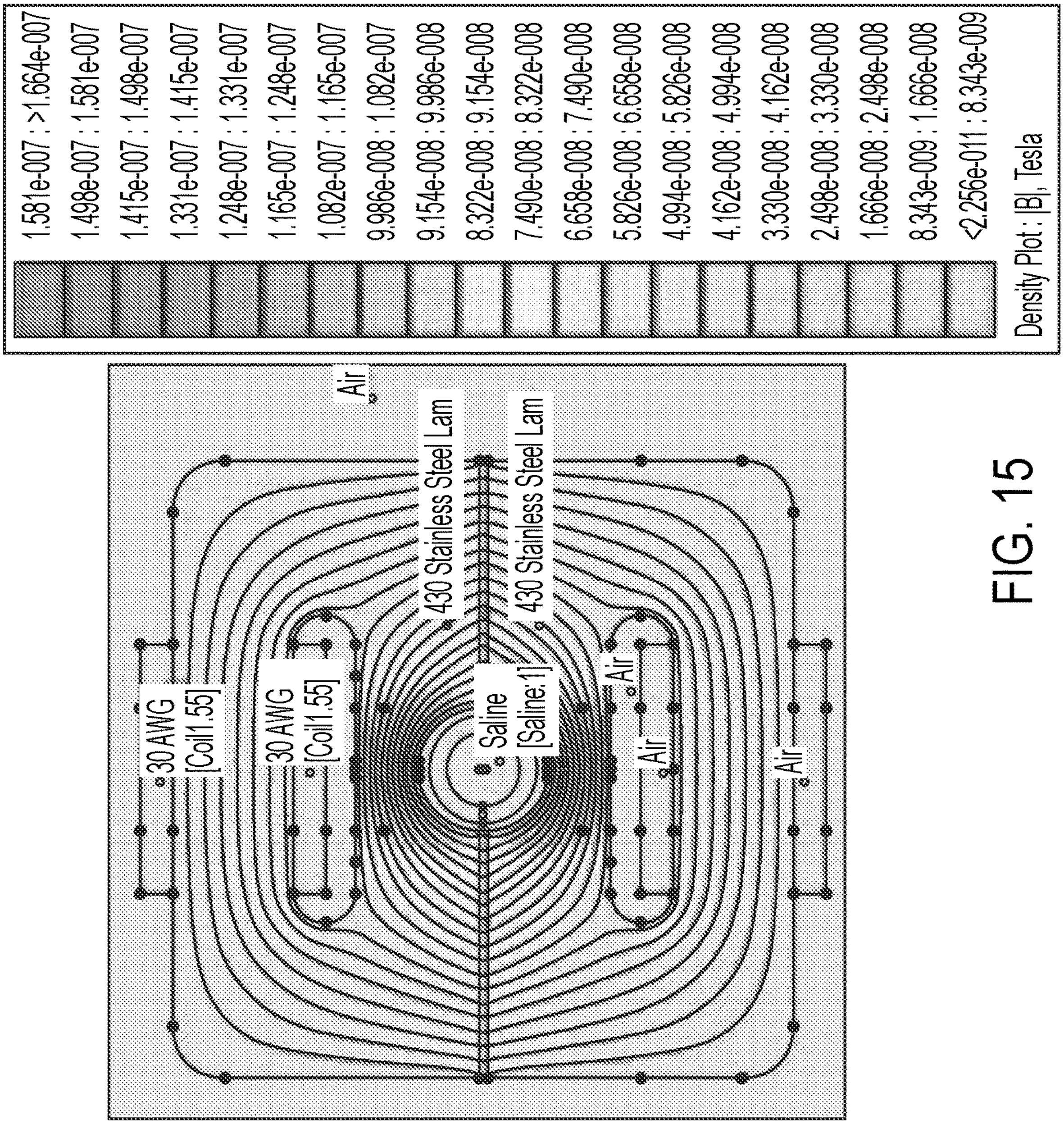
FIG. 15 illustrates a cross-section view of a square toroid with a single air gap and a graphical depiction of a magnetic field according to embodiments of the disclosed subject matter.

FIG. 15 illustrates a cross-section view of a square toroid with a single air gap and a graphical depiction of a magnetic field according to embodiments of the disclosed subject matter. The following results were observed:

Air Gap 1: 0.020"

Air Gap 2: 0.000 (none)

Fluid Current: 50 μA

Coil Voltage: 63.1 nV

Primary Inductance: 154 nH

Figure 16:
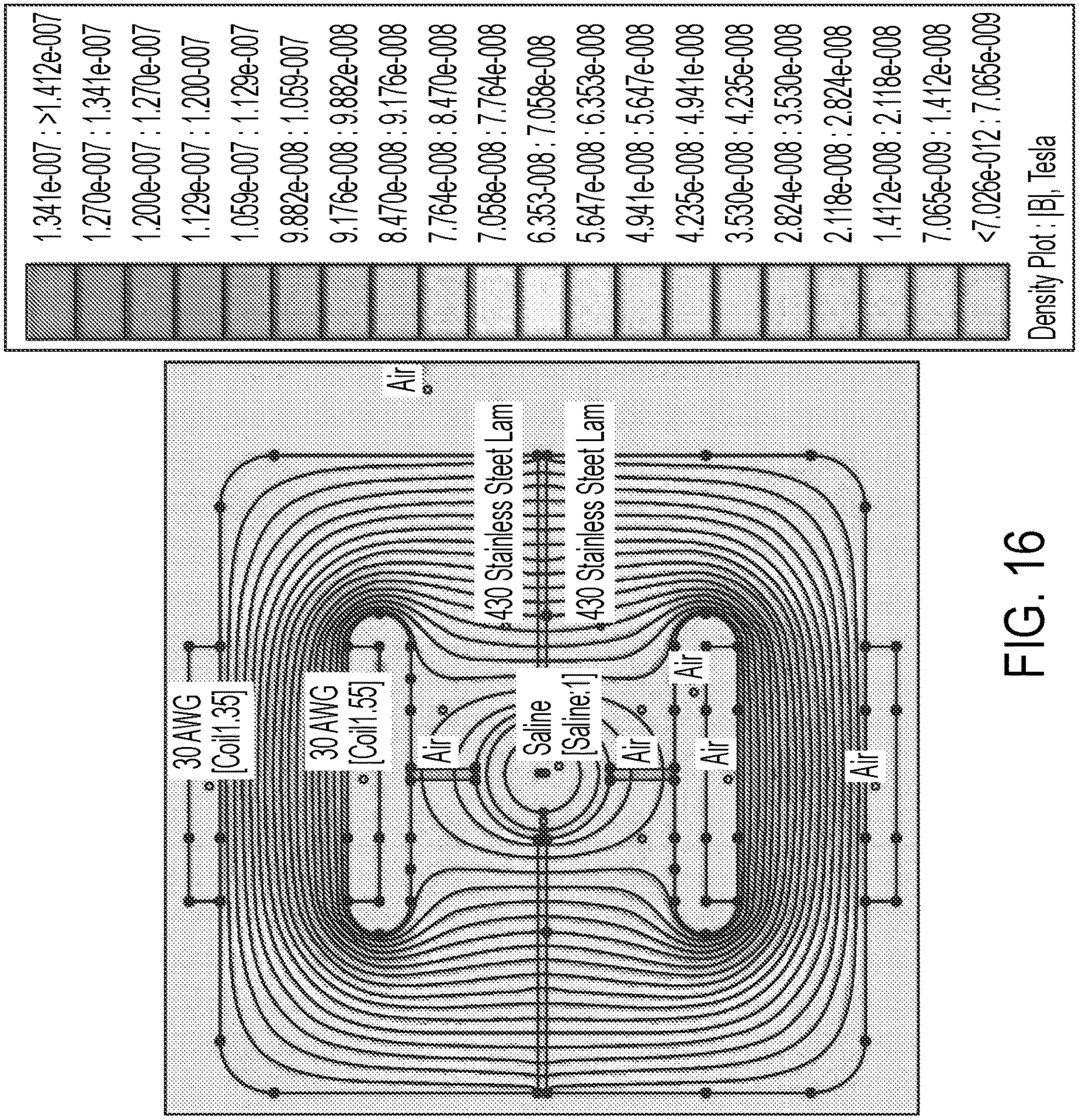
FIG. 16 illustrates a cross-section view of a square toroid with two air gaps and a graphical depiction of a magnetic field according to embodiments of the disclosed subject matter.

FIG. 16 illustrates a cross-section view of a square toroid with two air gaps and a graphical depiction of a magnetic field according to embodiments of the disclosed subject matter. The following results were observed:

Air Gap 1: 0.020"

Air Gap 2: 0.016

Fluid Current: 50 μA

Coil Voltage: 114.6 nV

Primary Inductance: 127.9 nH

Figure 17:
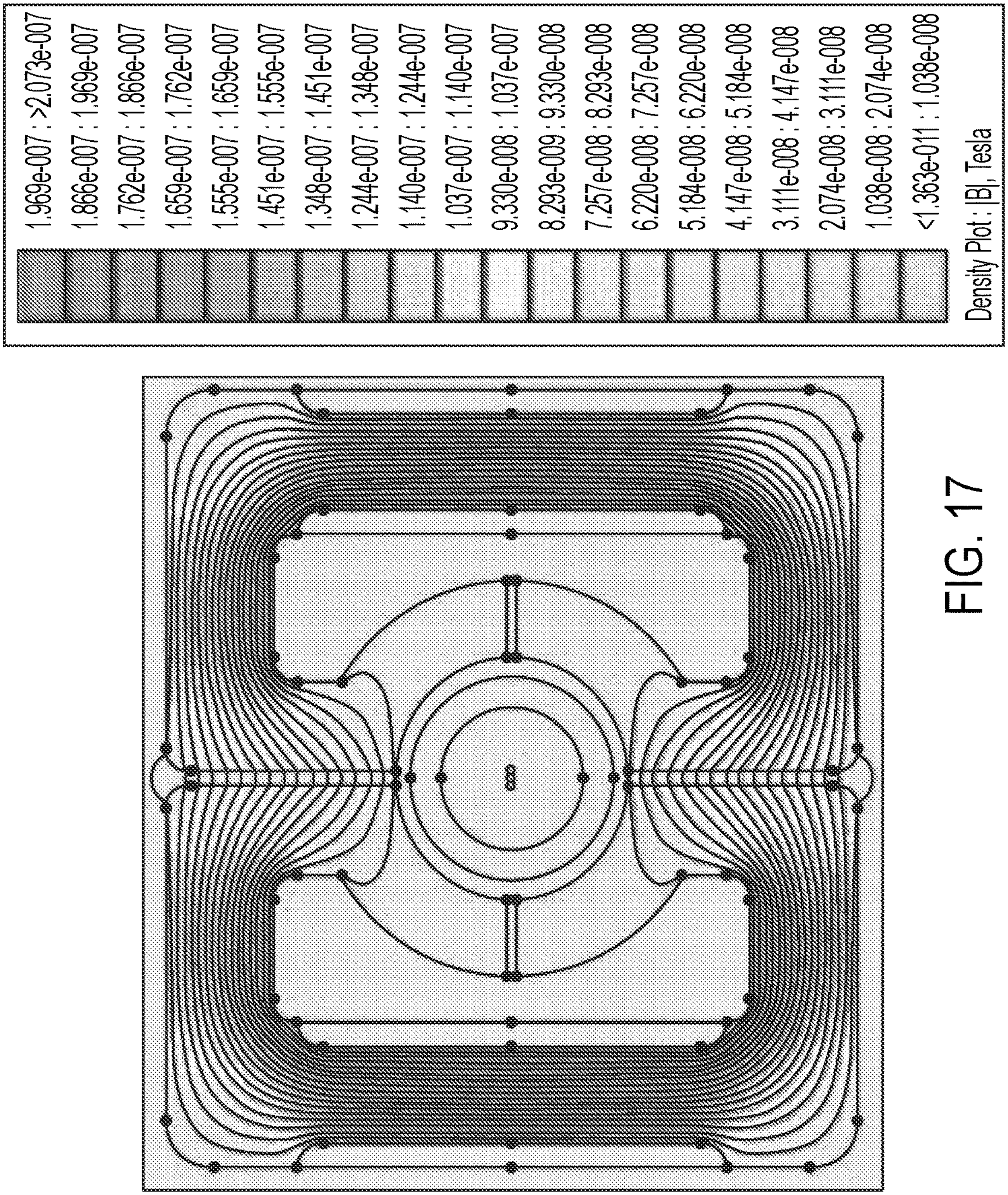
FIGS. 17-20 illustrate cross-section views of a square toroid and graphical depictions of magnetic fields based on some embodiments.
Figure 18:
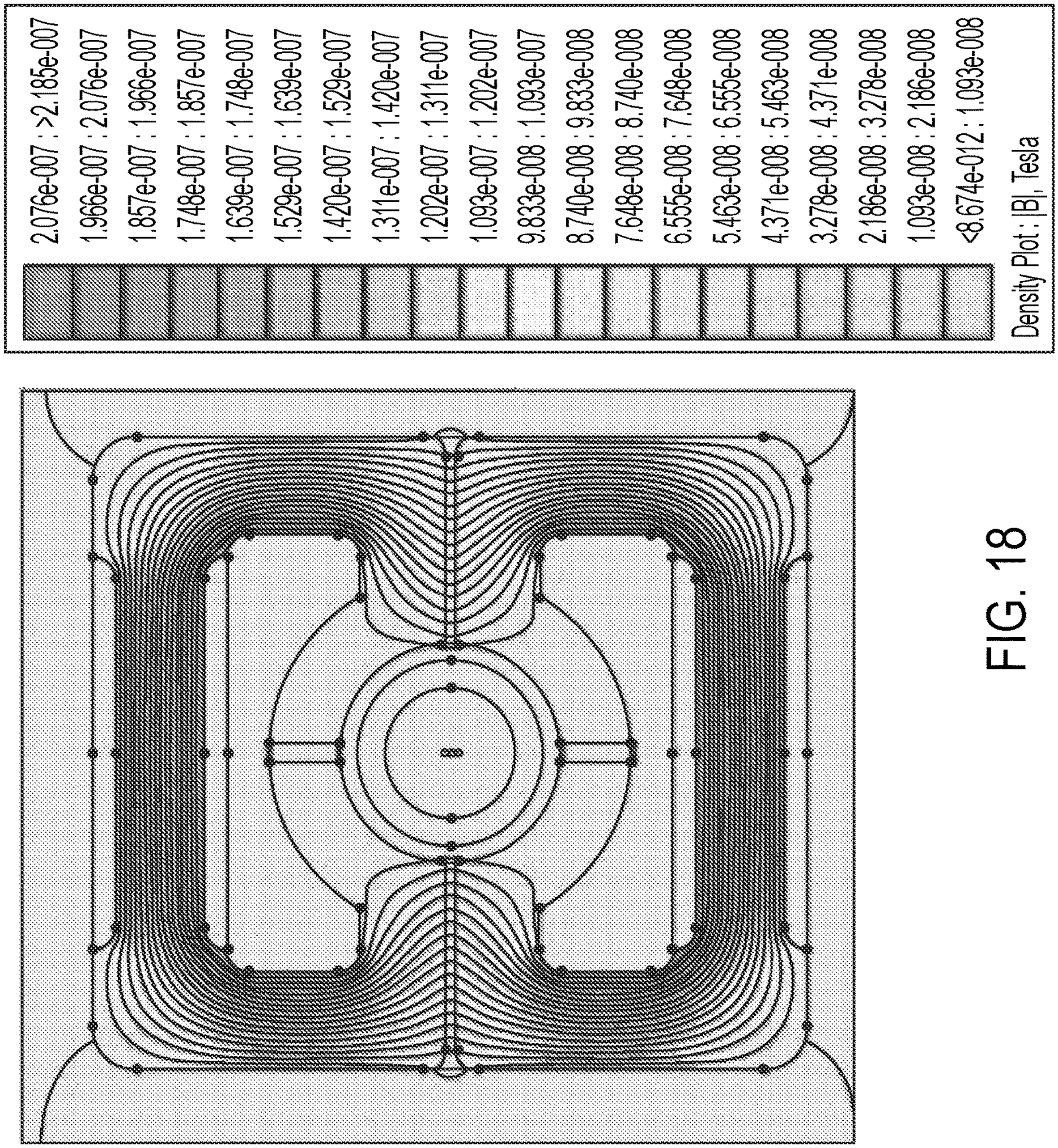
Figure 19:
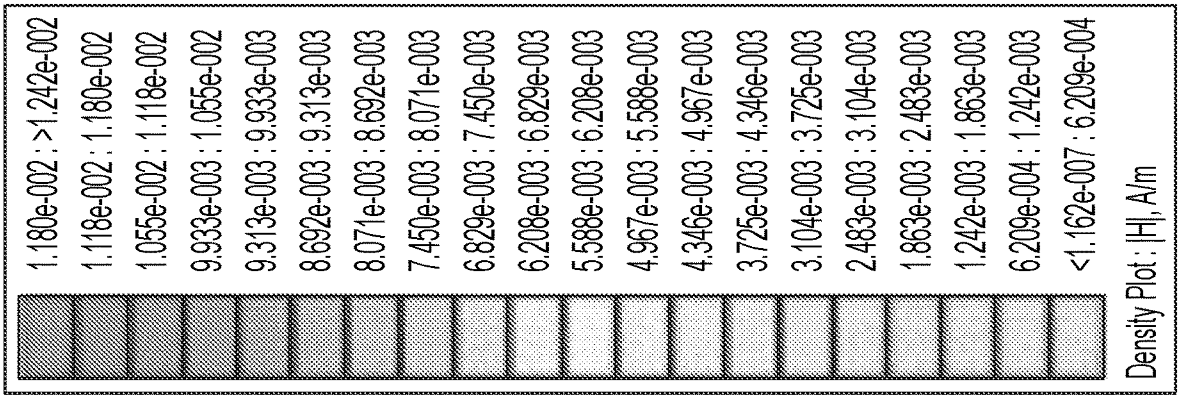
Figure 19:
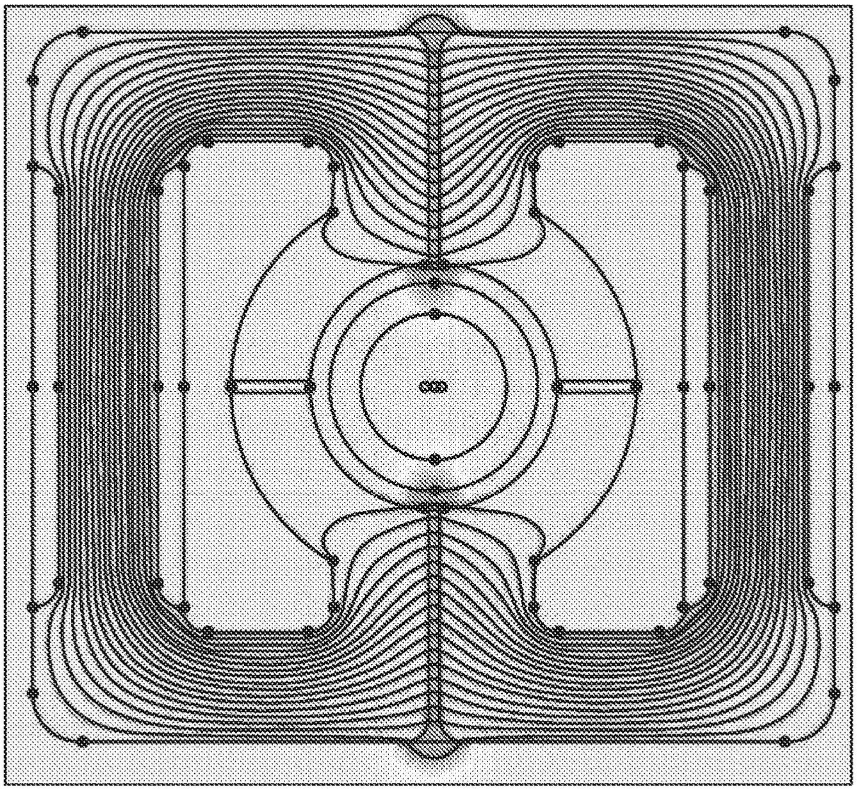
Figure 20:
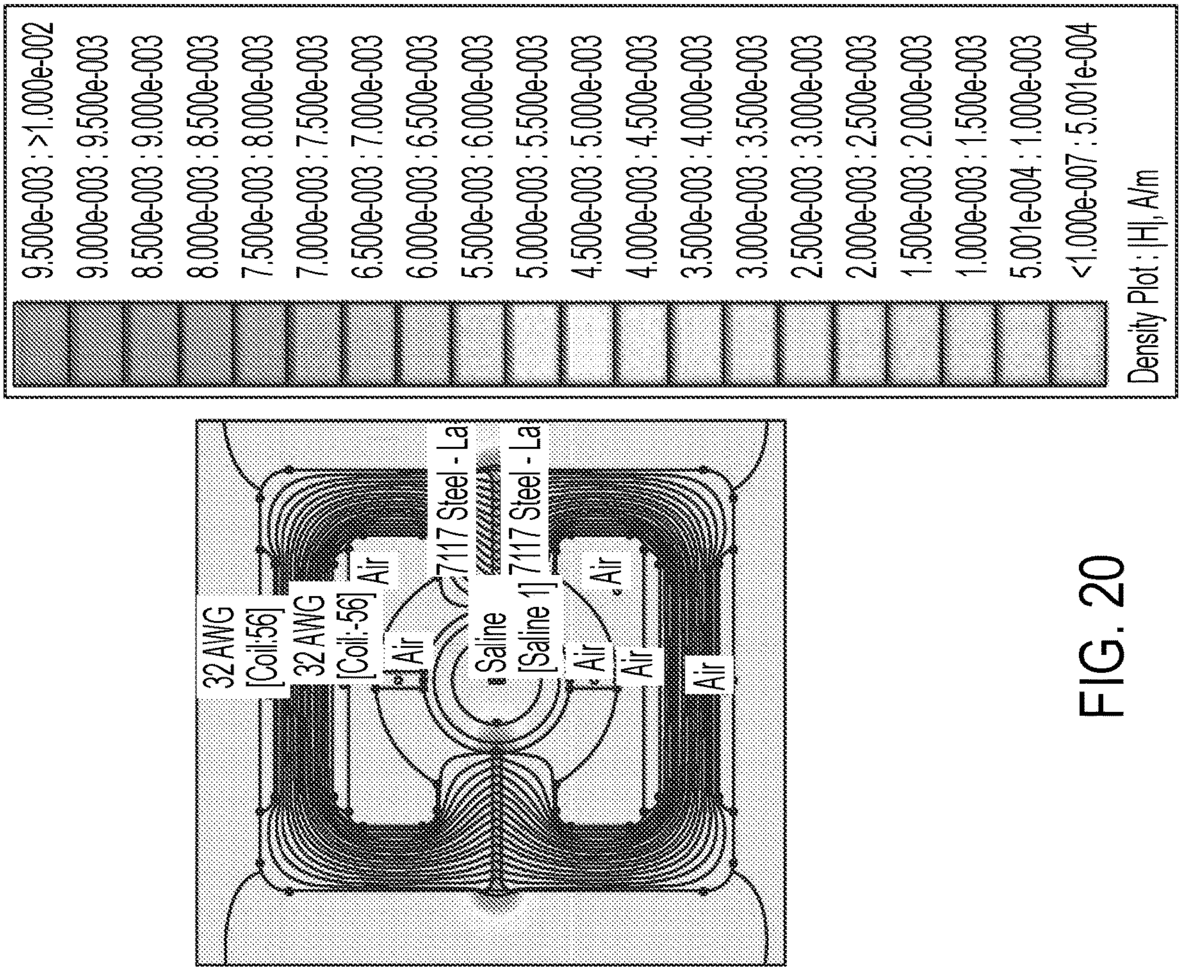

FIGS. 17-20 illustrate cross-section views of a square toroid and graphical depictions of magnetic fields based on some embodiments. FIG. 17 illustrates the B magnetic field (density plot: Tesla) for a square toroid with a 0.012 air gap based on some embodiments. FIG. 18 illustrates the B magnetic field (density plot: Tesla) for a square toroid with a 0.28 air gap based on some embodiments. FIG. 19 illustrates the H magnetic field (density plot: amps/meter) for a square toroid with a 0.012 air gap based on some embodiments. FIG. 20 illustrates the H magnetic field (density plot: amps/meter) for a square toroid with a 0.28 air gap based on some embodiments.

FIG. 21 illustrates a current sensor mechanical design according to embodiments of the disclosed subject matter. Embodiments of the patient leakage current sensor ("PLCS") design have the following dimensions for either the upper half or the lower half:

Length: 0.900"

Heigth: 0.500"

Width: 0.300"

Figure 22:
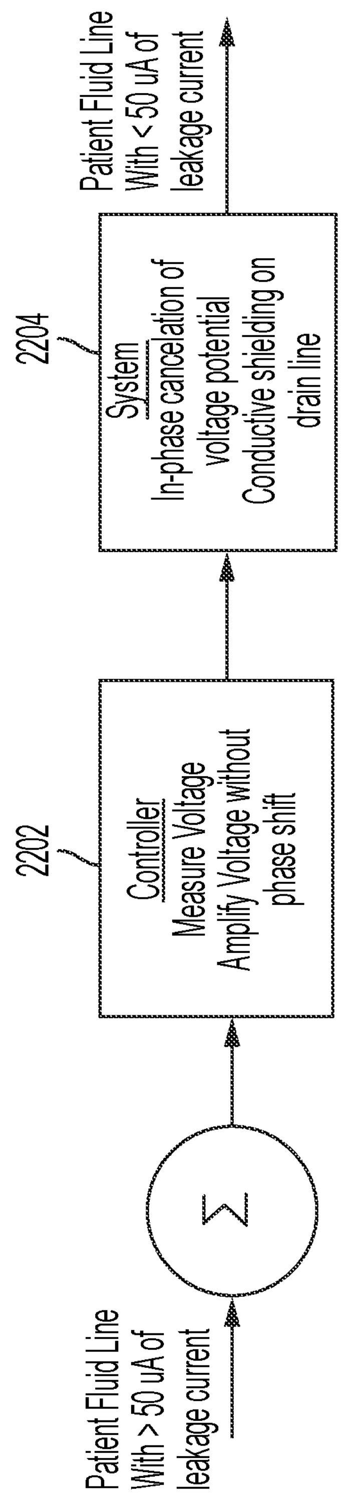
FIG. 22 illustrates an alternative open loop system for reducing current flowing in a conductive fluid according to embodiments of the disclosed subject matter.

FIG. 22 illustrates an alternative open loop system for reducing current (e.g., leakage current) flowing in a conductive fluid according to embodiments of the disclosed subject matter. Embodiments include an open loop technique that implements a drain line with a metal shield. A patient fluid line, such as a blood line, can include leakage current, for example due to an electrified patient. Controller 2202 and system 2204 can measure the voltage in the patient fluid line (e.g., blood line). In some embodiments, the voltage in the fluid line can be sensed using a voltage sensing coil and/or the current in the fluid line can be sensed using a current sensing toroid. Controller 2202 and system 2204 can amplify or decrease the voltage, as needed, (without phase shift) and perform an in-phase cancelation of voltage potential.

Figure 23:
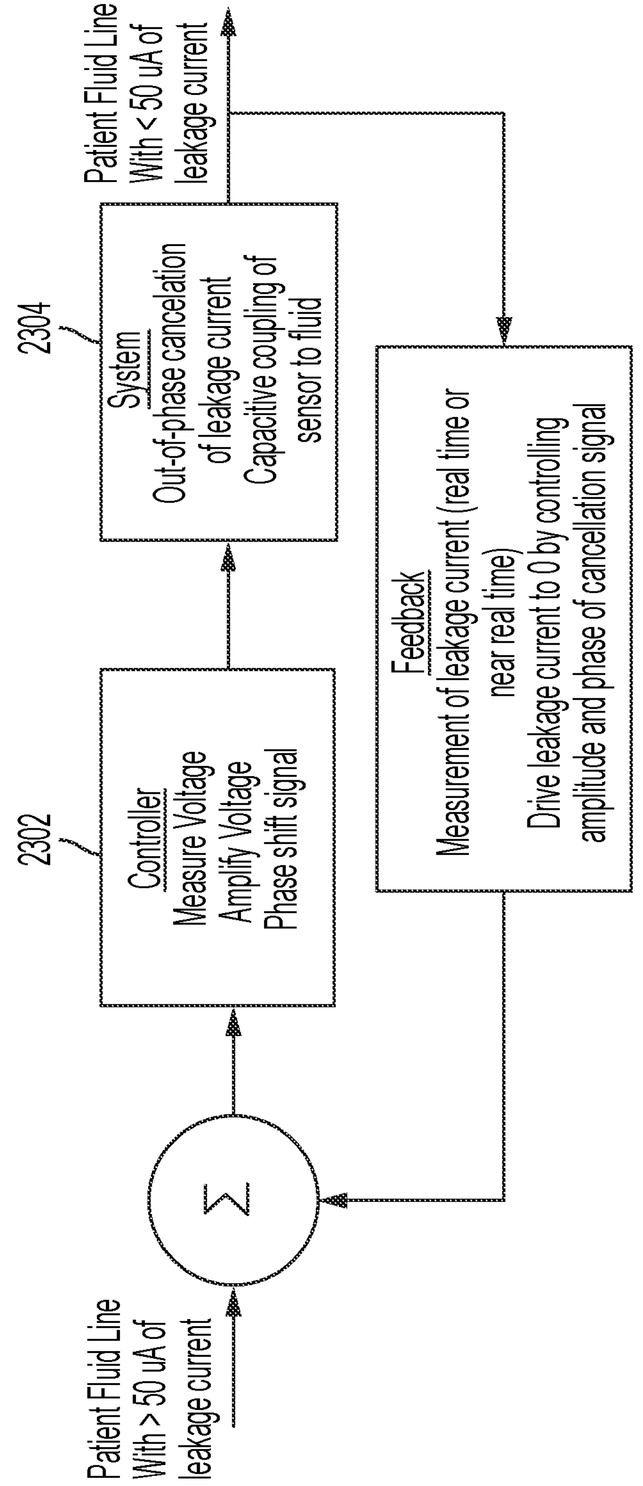
FIG. 23 illustrates an alternative closed loop system for reducing current flowing in a conductive fluid according to embodiments of the disclosed subject matter.

FIG. 23 illustrates an embodiment of a closed loop system for reducing current f (e.g., leakage current) lowing in a conductive fluid according to embodiments of the disclosed subject matter. Embodiments include a closed loop technique that implements a capacitive coupled driver capable of driving voltage into fluid. In embodiments, a contact electrode as described below is used to induce an appropriate voltage in a fluid line to cancel current flowing thorough that fluid line. A patient fluid line, such as a blood line, can include leakage current, for example due to an electrified patient. Controller 2302 and system 2304 can measure the voltage in the patient fluid line (e.g., blood line), amplify voltage or reduce the voltage, as needed, and/or phase shift voltage. In some embodiments, the voltage in the fluid line can be sensed using a voltage sensing coil and/or the current in the fluid line can be sensed using a current sensing toroid. In some embodiments, controller 2302 and system 2304 can perform out of phase cancelation of leakage current using a capacitive coupling sensor to drive current into the conductive fluid. For example, controller 2302 and system 2304 can utilized real-time measurement of leakage current to drive a cancelation current using phase shift and voltage amplification. In some embodiments, the cancelation current can reduce the leakage current to a threshold level, such as 50 μA.

Figure 24:
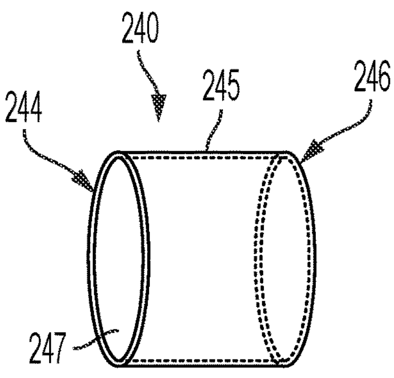
FIGS. 24-26 illustrate examples of a contact electrode according to embodiments of the disclosed subject matter.

All of the above embodiments can use contact-less transducers as described herein, or contact electrodes. Referring to FIG. 24, a contact electrode 240 may be made from a conductive material, such as stainless steel. However, other materials may be used. For example, a semi-conductive material, such as polymer impregnated with carbon, may be used, as described further below. All of the illustrated embodiments can be made from any of the disclosed materials. The contact electrode 240 has a first end 244 and a second end 246, which define the ends of the electrode. In embodiments, the electrode 240 can be a metal tube. The electrode may be manufactured by cutting a longer length to metal tubing into shorter segments. In embodiments, the length of electrode 240 is 1 cm. In other embodiments, the length is 2 cm, 3 cm, 4 cm, or greater than 4 cm. The length may be selected based on an expected leakage current, as the inner surface area 247 of the electrode determines the effectiveness of the electrode in sensing voltage or current and in inducing voltage or current in a fluid line. In embodiments, the length of the electrode is 1 inch.

Figure 27:
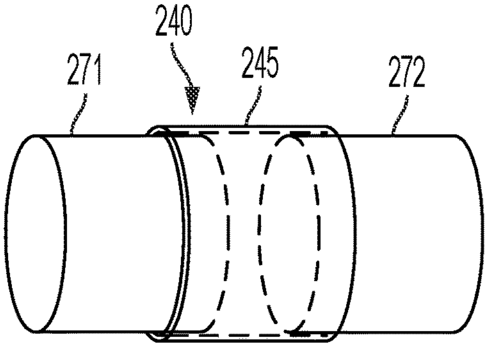
FIGS. 27-30 illustrate examples of a contact electrode in use with two tubing segments.
Figure 33:
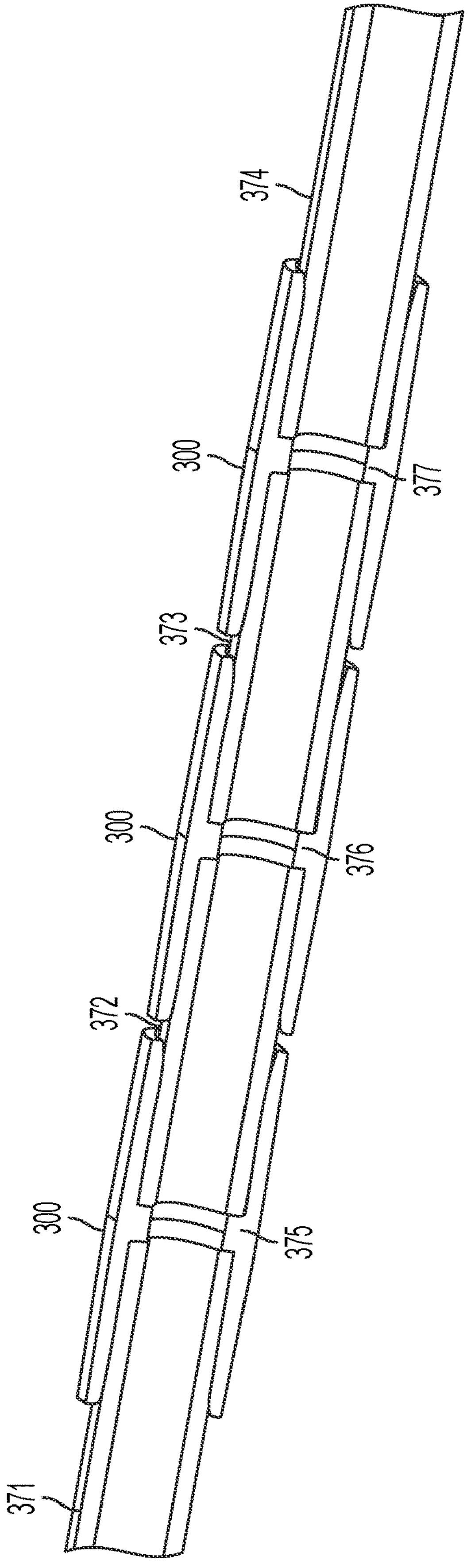
FIG. 33 illustrates an example of a contact electrode according to embodiments of the disclosed subject matter.

Electrode 240 may be used in the manner illustrated in FIG. 27, where two tubing segments 271 and 272 are inserted through openings 244 and 246 of the electrode 240. In this scenario, the entire outer surface 245 of electrode 240 is accessible and can be electrically coupled (e.g., by soldering or with a conductive clamp 301) to the leakage current cancellation system. However, the electrode 240 may be also used in the manner shown in FIG. 28, where the tubing segments 271 and 272 are inserted over the electrode's ends. To ensure that the tubing segments are securely attached to an electrode, an adhesive and/or heat welding can be used on the tubing segments. Although not visible in FIGS. 24 and 27, electrode 240 may have an internal rib, similar to the external flange 253, running around the internal circumference of the electrode. This rib may provide a surface against which tubing segments 271 and 272 may abut when they are inserted into the electrode 240 as illustrated in FIG. 27. An example of a rib 375, 376 and 377 is illustrated in FIG. 33.

Figure 25:
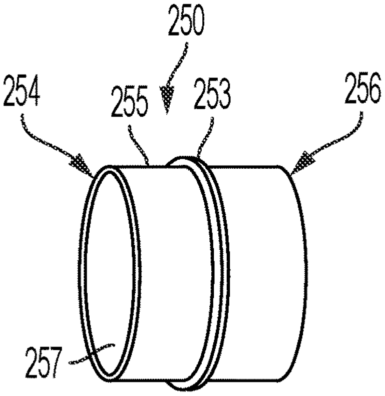

Referring to FIG. 25, another embodiment of a contact electrode 250 is shown. As noted above, electrode 250 can be made of the same materials as electrode 240. Electrode 250 has a first opening 254 and a second opening 256 which define the outer edges of the electrode. In embodiments, the entirety of electrode 250 is made of the same conductive material, so the outer surface 255 of the electrode 250 is conductively coupled to the flange 253 which rises radially out from outer surface 255.

Figure 28:
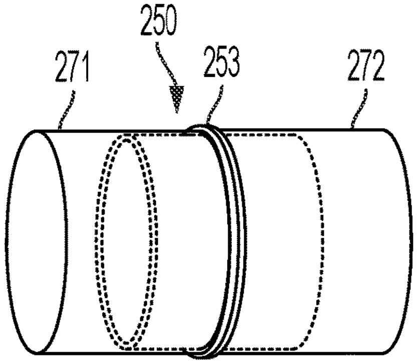

As shown in FIG. 28, the flange 253 provides a stopping region for tubing segments 271 and 272 when they are pressed onto the electrode 250. The tubing segments are pressed until they come into contact with the flange 253, ensuring a leak free and secure connection, while the flange 253 provides a location for a conductive connection to the leakage current cancelation system. Thus, a conductor such as a wire may be conductively coupled to the flange 253. As will be appreciated, the entire inner surface 257 of the electrode 250 is inside of the flow path between tubes 271 and 272. This maximizes the usage of the surface area of the electrode in contact with the fluid that flows through the flow path. As noted above, adhesives and/or heat welding may be used to secure the tubing segments 271 and 272 to the electrode.

Figure 29:
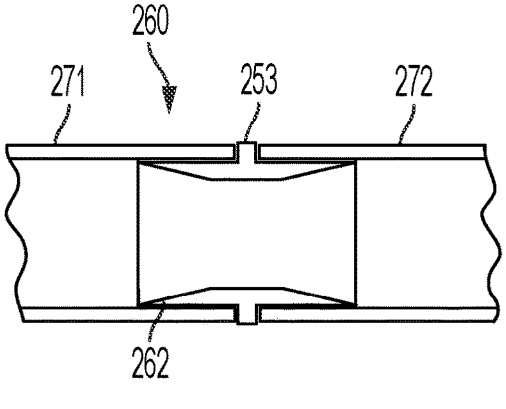

The flange 253 is illustrated as approximately the same height as the thickness of tubing segments 271 and 272, as shown in FIG. 29. This configuration makes the resulting combination of tubing segments and electrode(s) have a smooth surface that can be passed through openings sized to accommodate the tubing size and also to minimize kinks in the combined tubing.

In other embodiments, the flange 253 may be raised to have a greater height than the thickness of the tubing. In these embodiments, the resulting combination of tubing and electrode(s) will have a larger outer diameter than the tubing alone, which may be used in a clamp-like connector 301 that clamps onto the electrode to provide an electrical connection.

Figure 26:
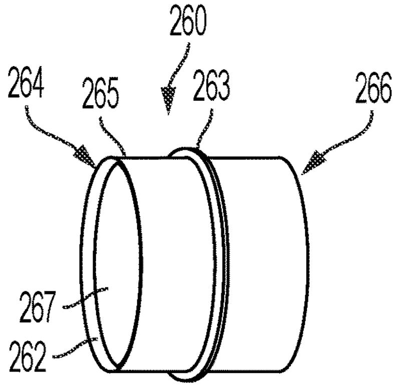

Referring to FIG. 26, and embodiment of a contact electrode 260 is similar to electrode 250, including an outer surface 265, an inner surface 267, and two ends 264 and 266. However, electrode 260 also has a beveled edge 262 at both openings, which is also illustrated in cross-section in FIG. 29.

Referring next to FIG. 29, the beveled edge 262 provides a gradual transition in inside diameter from the internal diameter of the tubing segments 271 and 272 to the smaller internal diameter of the electrode 260. When the fluid conveyed through tubing segments 271 and 272 is blood, any sudden transition in internal diameter may create flow irregularities that could damage (e.g., shear) blood cells. To mitigate this risk, the beveled edge 262 avoids abrupt transitions when electrode 260 is coupled to tubing segments.

Figure 30:
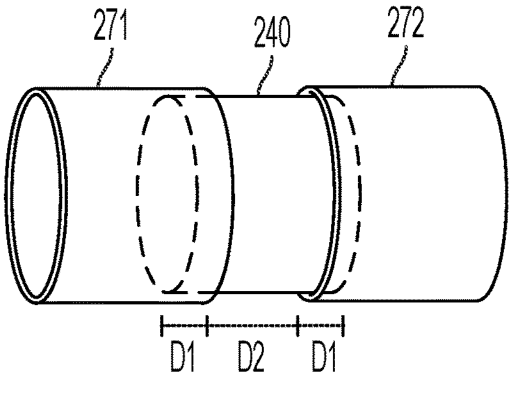

FIG. 30 illustrates another exemplary embodiment of tubing segment 271 and 272 interfacing with a contact electrode 240. In this embodiment, the tubing segments are positioned on the outside of the electrode 240, as shown in the figure. Dimensions a D1 a, D2 are indicated below the figure. D1 a represents the distance how far the electrode 240 is inserted into tubing segment 271 and 272. D2 represents the length of the exposed region of electrode 240. In an embodiment, distance D1 is one quarter of an inch, and the distance of the D2 is one half of an inch. Thus, in an embodiment, electrode 240 may be one inch long. Although these dimensions are not illustrated in FIGS. 24-29, it should be understood that the same dimensions may be used in any and all of these figures.

Figure 31:
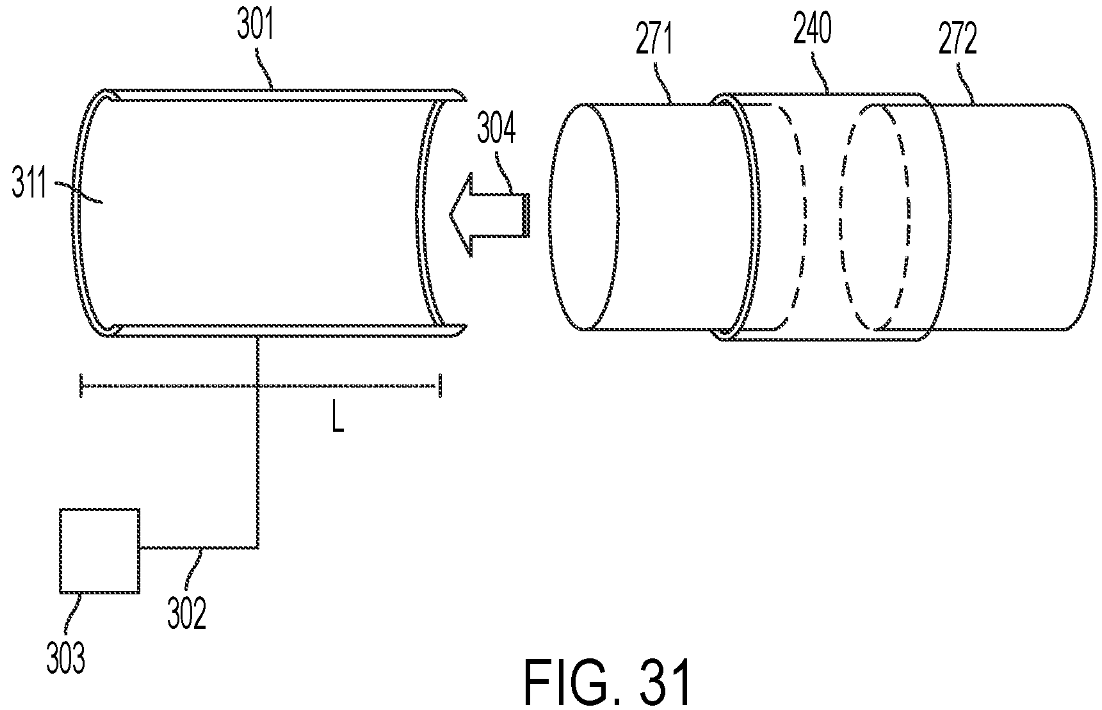
FIG. 31 illustrates an example of an electrode clamp in use with electrodes according to embodiments of the disclosed subject matter.

FIG. 31 illustrates an example of a clamp 301 which is designed to interface with any of the electrodes described herein. The clamp 301 may be constructed of a conductive material, such as copper, silver, gold, or other material with a conductive coating. In an embodiment, clamp 301 has an inner surface 311 which is sized and configured to receive electrode 240 as indicated by the arrow 304 in FIG. 31. The clamp 301 has a C-shaped profile to accommodate and securely hold a tubular object, such as an electrode. The clamp could have a different cross-sectional profile, such as three straight lines that would still allow a tubular object to be inserted and held securely and to ensure a conductive connection.

Once the electrode 240, and the tubing segments 271 and 272, are inserted into the clamp 301, an electrically conductive connection is established between electronic component 303 through a conductor 302. As will be understood, the electrode 240 can be pressed into the clamp 301 from multiple sides and directions, not only in the direction indicated by arrow 304. Although not illustrated in FIG. 31, clamp 301 may be present on the exterior or interior of a medical device 122. In embodiments, the medical device 122 has a fluid line organizer that holds various fluid lines in specified locations to avoid tangling and misuse of the lines. The fluid line organizer may include one or more clamps 301 to both hold the lines and keep the lines organized, and also to provide a conductive connection between electrodes coupled to the lines and the medical device 122.

The length indicated by the letter L of clamp 301 may be equal to or smaller than length D2. This allows clamp 30 one to be used with the embodiment illustrated in FIG. 30, such that the exposed outer surface of electrode 240 comes into full contact with the inner surface 311 of the clamp 301.

Figure 32:
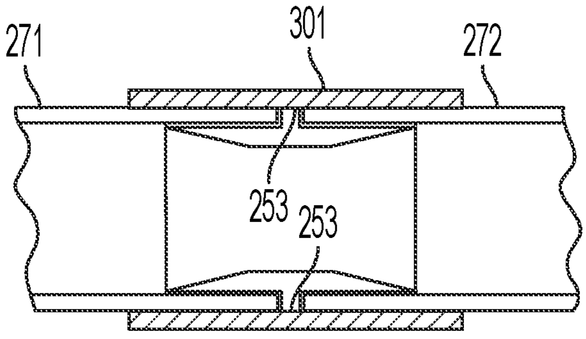
FIG. 32 illustrates a cross sectional view of an example of an electrode clamp in use with electrodes according to embodiments of the disclosed subject matter.

Referring to FIG. 32, a cross-sectional view of contact electrode 260 coupled to tubing segments 271 and 272, as inserted into clamp 301, is shown. As can be seen from the figure, the inner surface 311 is in contact with raised rib 253 of the electrode 260, thus creating an electrical connection.

FIG. 33 illustrates an exemplary embodiment of three electrodes 300 connected in series with tubing segments 371, 372, 373, and 374. In embodiments, the tubing segments have an internal diameter of 4.1 mm. Electrode 300 is made of a polymer that contains sufficient quantity of carbon to make the electrode conductive or semi-conductive (i.e., carbon impregnated polymer). In embodiments, the material from which electrode 300 is made is a mixture of polyvinylchloride (PVC) and powdered carbon. The carbon may be a colloid suspended in the polymer material.

In embodiments, the electrode 300 will be an integral part of the patient bloodlines of a medical treatment machine, such as a kidney dialysis machine. As illustrated in FIG. 33, three electrodes 300 are spaced apart from each other. The spacing between the electrodes 300 is selected so as to create a voltage drop between two adjacent electrodes. The spacing may be wide enough to produce a usable differential voltage signal for sensing and control of the patient leakage current cancellation. The length of the electrode 300 is selected to be long enough to create a double layer capacitor with a value greater than 1000 times the input amplifier sensing capacitor. In embodiments, the input amplifier sensing capacitor will be small enough to limit of the input sensing current to be less than 5.0 micro-amps. In embodiments, the capacitance of the input amplifier sensing capacitor will be less than or equal to 100 pF (pico-farad) for 132 VAC (RMS) single fault condition. Thus, the double layer capacitor which is formed by the electrode 300 will have a capacitance greater than 100 nF (nano-farad) or 0.10 μF (micro-farad). In embodiments, the DC electrical resistance from the outside surface of electrode 300 the inside surface (at rib 375) is less than 10,000 ohms. The internal diameter at the inside surface at rib 375 may be the same as the internal diameter of the tubing segment (e.g., 371, 372) to which the electrode 300 is connected. In embodiments, the internal diameter is 4.1 mm.

Figure 34:
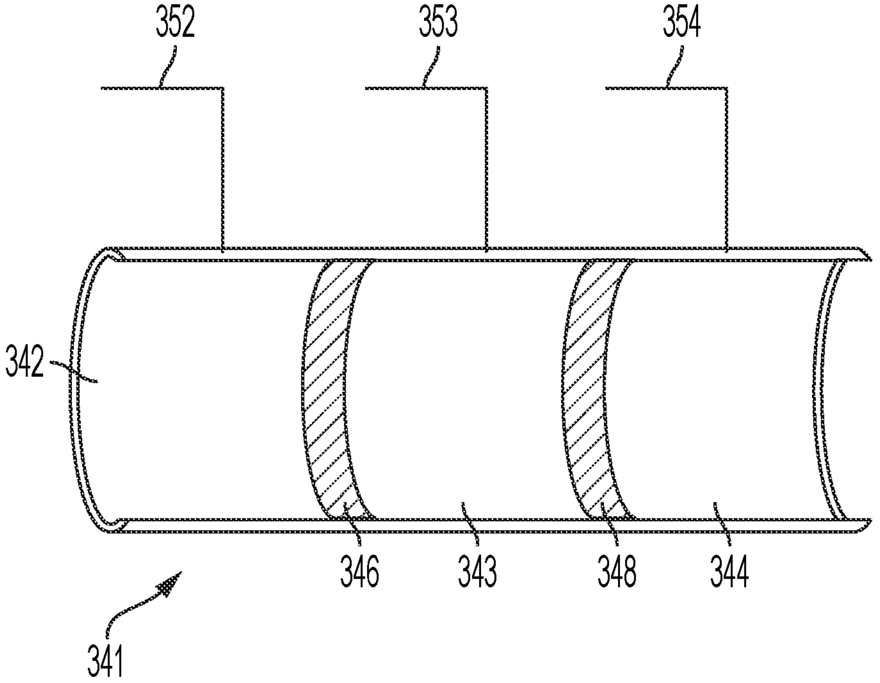
FIG. 34 illustrates an example of an electrode clamp with multiple contact regions according to embodiments of the disclosed subject matter.

The one or more electrical clamps 301 of FIG. 31 may be used with the electrodes 300. For example, one respective electrical clamp 301 may be provided for each individual electrode 300. In other embodiments, for example as illustrated in FIG. 34, electrode clamp 341 may be large enough to accommodate three of the electrodes 300. Electrode clamp 341 includes three conductive regions 342, 343, and 344. These separate conductive regions are configured to come into contact with respective ones of electrodes 300 as shown in FIG. 33. The conductive regions are separated by insulating regions 346 and 348, and each conductive region has a respective electrical lead 352, 353, and 354. The electrical leads may connect to circuitry as described below. It will be understood that the electrode clamp 341 may be used with the carbon filled polymer electrodes as well as other types of electrodes such as the stainless-steel electrodes discussed above.

In embodiments, the electrode 300 has a length of 1 inch as measured along its principal axis. The electrode 300 may have a resistance value lower than 10,000 Ohms as measured between the leakage current cancellation system and the fluid in flow path.

In embodiments, the carbon content of the polymer electrode 300 includes a powder that is passed through 325 mesh (so called 325 mesh carbon powder). In other embodiments, the carbon component includes powder that is passed through 8×50 mesh (so called 8×50 mesh carbon powder). In further embodiments, the carbon component includes a mixture of 325 mesh carbon powder and 8×50 mesh carbon powder. In embodiments, the carbon content is 15% to 35% of the total volume of the electrode 300, such that a polymer makes up the remaining volume.

In embodiments, the resistance value as measured between two adjacent electorates 300, when the tube between the electrodes (e.g., tube segment 372) is filled with a fluid with the resistivity value of saline or human blood, is 1.5 KΩ (kilo-ohms). In FIG. 34, this would be the resistance measurement between electrical leads 352 and 353 when the electrode and tube assembly of FIG. 33 is inserted into the electrode clamp 341.

In embodiments, multiple copies of electrode 300 may be permanently, or a semi permanently, joined together at the time of manufacture. This would result in a single unitary structure with multiple contact the regions inside that will come in contact with the fluid that flows through the interior of the electrode. For example, the embodiment illustrated in FIG. 33 may be constructed as a single body embodiment if the gaps which are pointed to by reference numbers 372 and 373 are filled with a nonconductive material, such as the material from which tubing segments 371 and 374 are made. Such an exemplary embodiment may then be used to connect the single body, multi-contact, electrode to two tubing segments such as 371 and 374.

Figure 35:
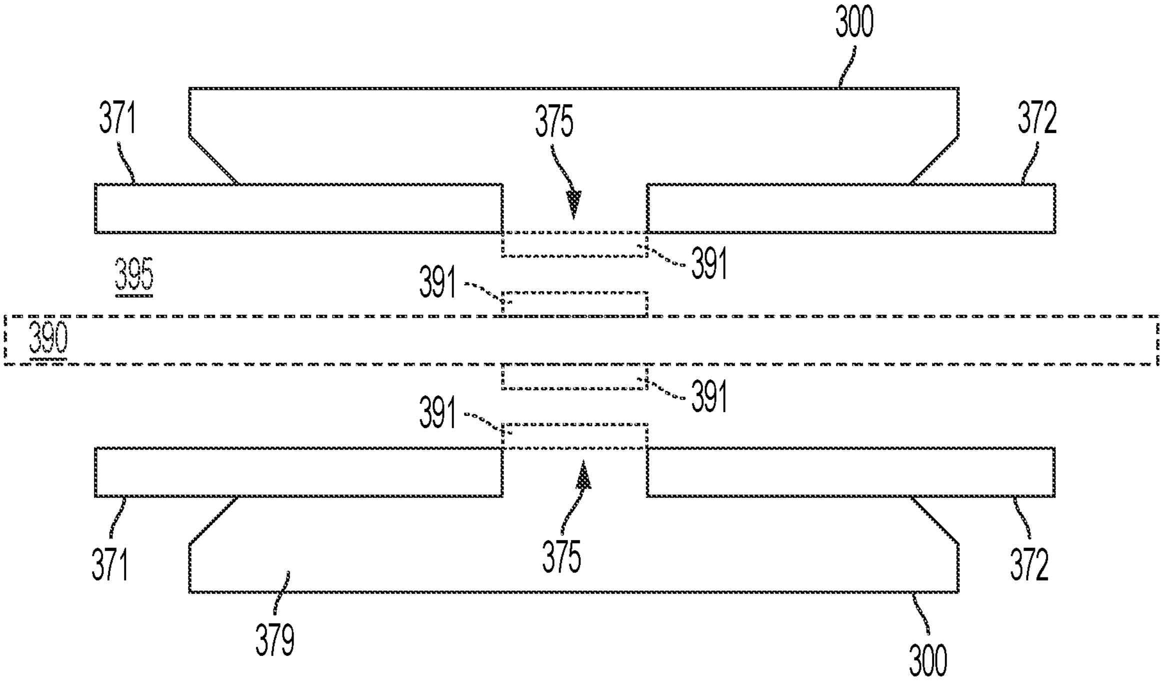
FIG. 35 illustrates an example of a double layer capacitor that is formed by electrodes according to embodiments of the disclosed subject matter.

Referring to FIG. 35, a cross-section of electrode 300 taken down the middle of the tubing is shown to help explain schematically the double layer capacitance that results from this particular arrangement. The open space that is shown between tubing segment 371 and 372 and the opposed portions of that is tubing is filled with a fluid 395, such as blood. The inner surface of rib 375 will come into contact with the fluid flowing through the tubes. This inner surface forms a double layer capacitor. The inner surface functions as a conductor in a coaxial capacitor. In this coaxial capacitor, the inner conductor is the conductive fluid (e.g., blood) flowing through the tubing. Because the inner conductor is a fluid, an interface 391 will be created (on the order of nanometers thickness) at the inner surface at each of the ribs 375, 376, and 377 and also at the boundary of the conductive component 390 of the fluid 395. The interface is a pure dielectric due to the non-conductive components of the fluid. An electric a double layer appears at the interface 391 between surface of rib 375 and the conductive fluid 390. At this interface, two layers of charge with opposing polarity form, one at the surface of the electrode, and one in the conductive fluid. These two layers are separated by a thin layer which is indicated as 391 in FIG. 35. When a voltage is applied to the electrode 300, two layers of polarized ions are generated at the electrode interfaces. One layer is within the solid electrode (at the surface of rib 375). The other layer, with opposite polarity, forms from dissolved and solvated ions distributed in the liquid 390 that have moved towards the polarized electrode. These two layers of polarized ions are separated by a layer (indicated as 391) that acts as a dielectric and is extremely thin (e.g., 0.1 to 10 nm). The extremely small thickness of this layer contributes to the ability to obtain a large capacitance in a very small device, much larger than with a conventional capacitor.

In embodiments, the capacitance of this double layer capacitor is 0.1 μF or greater. The overhanging region 379 indicated in FIG. 35 also results in a capacitance between a portion of electrode 300 and the conductive fluid on the other side of tubing 371 or 372. However, because the tubing has a much thicker side wall than the interface layer 391 described above, the resulting capacitance is much smaller for this part of the electrode 300. In fact, this small capacitance is undesirable, because the total capacitance at the electrode 300 is the result of a series connection between the capacitance due to the overhang 379 and the double layer capacitor formed at the surface of region 375. Therefore, it is desirable to reduce the length of overhang region 379 to increase the total capacitance of the electrode 300. The overhang region 379, however, it is beneficial for physical attachment purposes as it may have barbs on the inner surface (not illustrated) and may be used for solvent bonding the tubing segments to the electrode 300.

Figure 36:
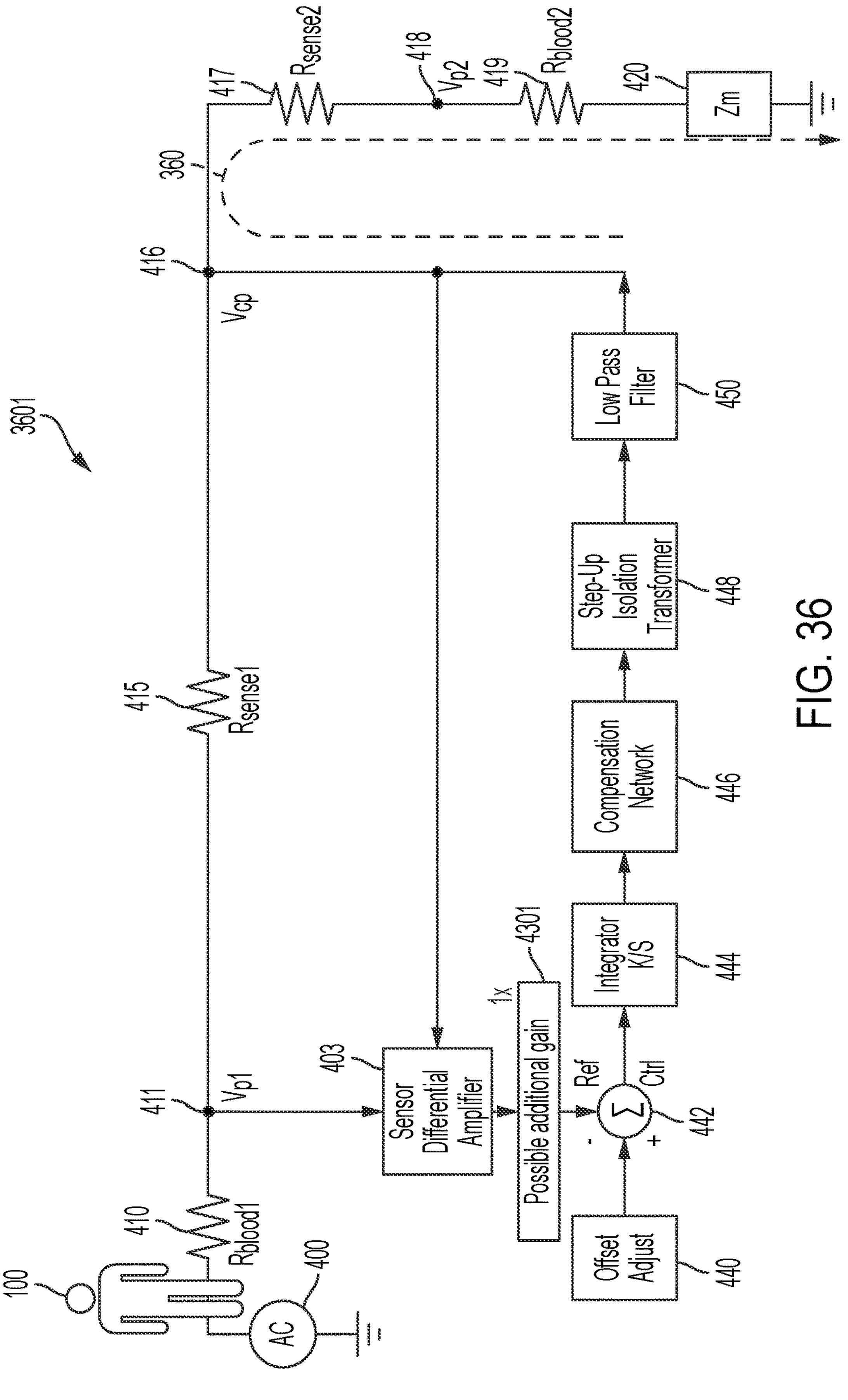
FIG. 36 illustrates an example of a tracking circuit according to embodiments of the disclosed subject matter.

Referring next to FIG. 36, an embodiment of a control and driving circuit 3601 for reducing patient leakage current is illustrated. An embodiment of the circuit mitigates patient leakage current that is assumed to be AC current at 50-60 Hz. In an embodiment, the acceptable patient leakage current is less than 150 μA or even less than 50 μA when the patient is subjected to an excitation voltage of 132 VAC (RMS). In embodiments, when the excitation of voltage is 264 volts (RMS), the patient leakage current is a less a than 300 μA. The embodiment of FIG. 36 can be considered a tracking generator that tracks the voltage with which the patient 102 is energized, and generates a compensating voltage to cancel or reduce leakage current from the patient to ground.

Patient 102 is connected through a patient blood tubing set to a medical treatment device 122 represented as impedance Zm connected to ground at 420. One end of the patient blood tubing set is connected to the patient access (arterial and/or venous) and the other end enters a medical treatment machine 122 (e.g., hemodialysis machine). If the patient 102 is accidently electrified via a single fault condition (as modeled by AC source 400), current may flow through the patient's blood lines, arterial and venous, to the dialysis machine and electrically (capacitively) couple to earth ground and provide an electrical current path to the excitation voltage source. This current may be reduced by employing a circuit that senses the current and actively reduces it.

The circuit 3601 uses a control loop which senses the voltage $V_{p1}$ at the patient using any electrode or transducer described above. To measure the AC current flow through the blood line connected to the patient, it is possible to measure a voltage with two electrodes/transducers at two positions along the blood line, because the spacing between two sensors has a known resistance value (derived from the conductivity of the fluid in the fluid line, the length, and the cross section of the fluid line). Thus, a differential voltage across a sense resistor, created by two electrodes according to any of the embodiments described above in a conductive fluid path, is measured and from this differential voltage a current can be calculated. By placing two electrodes in a tube containing an electrically conductive fluid and separating them by a distance, an electrical resistor will be formed as noted above. Therefore, when electrical current flows in the conductive fluid, a voltage drop will be created across the electrodes. The voltage across the electrodes is directly proportional to the current flowing in the tube. The electrical current can be either direct current (DC) or alternating current (AC). In embodiments, the voltage across $R_{sense1}$ is 15 mV (RMS), and the total gain from Ref to $V_{cp}$ is 10,000, so that the voltage at $V_{cp}$ is approximately 132 V AC (RMS).

FIG. 36 represents a schematic circuit diagram which models the behavior of the fluid lines with electrodes and various sensing and driving elements. Three electrodes, according to any of the embodiments described above, per blood line (arterial and venous) sense and cancel the electrical leakage current. Points Vp1 at 411, Vcp at 416, and Vp2 at 418 represent the locations of the three electrodes, respectively.

The two electrodes closest to the patient (411, 416), on each blood line, are used to sense the leakage current. Because electrodes 411 and 416 are separated by a length of tubing that is filled with a fluid (e.g., blood), there is a finite resistance between the two electrodes, represented by Rsense1. The voltage difference across $R_{sense1}$ is used as input to the sensor a differential amplifier 430.

Referring again to FIG. 36, the output of sensor differential amplifier 430 is the difference between voltage at $V_{cp}$ and $V_{p1}$ and is provided to a summing unit 442 as a negative value (i.e., inverted). The summing unit 442 may be a digital device or an analog one such as an operational amplifier connected in a summing configuration.

In embodiments, the differential amplifier 430 receives as input 1.5 millivolts RMS, due to the difference between the voltage at $V_{cp}$ and $V_{p1}$. In embodiments, the differential amplifier 430 includes a transformer as illustrated in FIG. 37.

Figure 37:
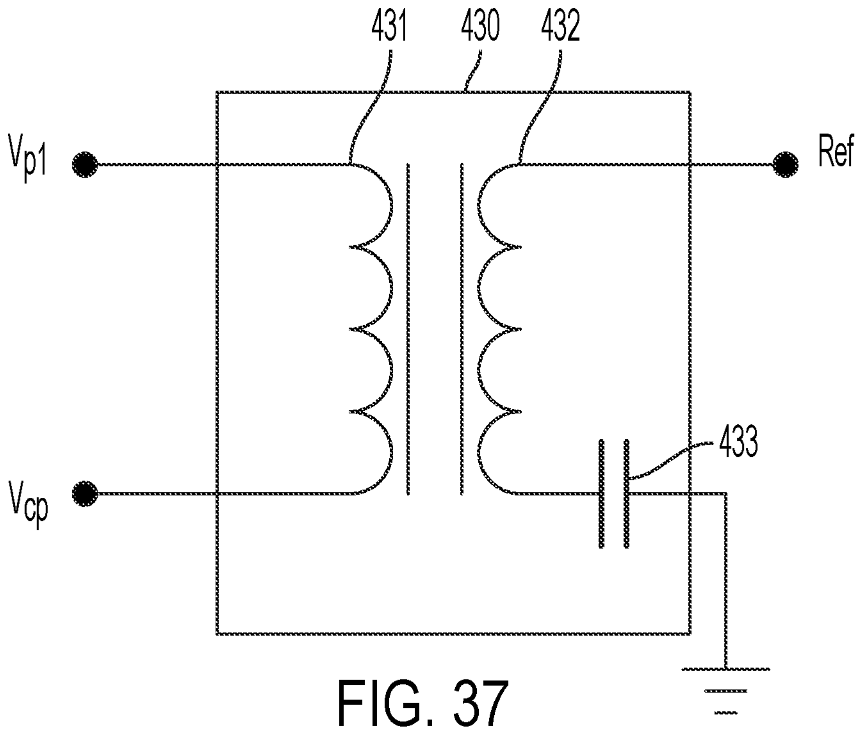
FIG. 37 illustrates an example of a differential amplifier design according to embodiments of the disclosed subject matter.

Referring to FIG. 37, the differential amplifier 430 may include a transformer with primary winding 431 in a secondary winding 432. The primary winding 431 is connected to two electrodes indicated as $V_{p1}$ and the $V_{cp}$. The secondary winding is connected to the summing circuit 442 with the output identified as Ref. This output is single ended, thus the second connection of the secondary winding is connected to ground through capacitor 433. In embodiments, the gain of the sensor differential amplifier 430 is one, but it may be also greater. The gain is controlled by selecting the number of windings in the primary winding 431 and the secondary winding 432. The capacitor 433 helps provide stability when the gain is increased.

Figure 38:
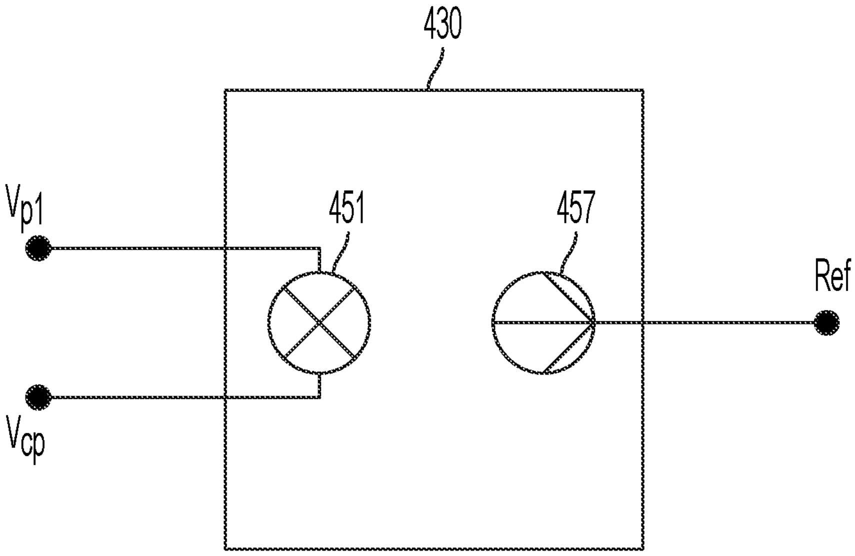
FIG. 38 illustrates another example of a differential amplifier design according to embodiments of the disclosed subject matter.

Referring to FIG. 38, the differential amplifier 430 may include a light source 451 which is driven by the differential voltage between Vcp and Vp1, and an optical sensor 452 which detects the light output, and outputs a voltage representative of the measurement. In embodiments, the light source is an incandescent lightbulb.

When the patient 102 is energized by an alternating current voltage, e.g. at 50 or 60 Hz, the output of the sensor differential amplifier 430 will be a sinewave at the frequency of the signal that energized the patient (i.e., 50-60 Hz). The summing unit 442 also receives as input an offset value which is provided by the offset adjustment 440. In embodiments, the offset may be 0 V.

The offset adjustment 440 may be a sine wave generator with a controllable amplitude, frequency, and phase.

The output of summing unit 442 is provided to integrator 444, which provides additional gain to the signal. In embodiments, the gain of integrator 444 is 10 to 20. The integrator 444 may be an operational amplifier circuit, or a digital integrator.

The output of integrator 444 is provided as input to compensation network 446. The compensation network 446 adds poles and zeros to the control loop to provide stability over the bandwidth of operation. In embodiments, the compensation network 446 is made of analog elements. In embodiments, the compensation network 446 includes resistors and capacitors with values selected to provide poles and zeros at frequencies that maintain stability of the gain loop, without digital components. In other embodiments, the compensation network 446 includes digital components. The compensation network 446 may provide additional gain on the order of 10-50×.

The output of the compensation network 446 is provided to a step-up isolation transformer 448, which provides additional gain between 10× and 16×. The output of the transformer 448 is provided to a low pass filter 450 which cleans up the amplified signal (e.g., a sine wave at 50-60 Hz) and outputs it to the electrode 416 at $V_{cp}$.

The output signal of low pass filter 450 includes alternating current which flows along the current path 360 illustrated in FIG. 36 as a dashed line. The current path starts at electrode 416 and continues through a tubing segment which has a quantity of fluid in it and is represented as resistor 417 with value Rsense2, through the third electrode 418, and through a final segment of tubing which if filled with fluid and represented as resistor 419 with resistance value Rblood2. As a result, the current that flows through Rblood1 (i.e., the current flowing through the patient) is very low, below 50 μA.

Element 420 represents the impedance Zm of the treatment machine (e.g., medical equipment 122) to ground. In embodiments, Zm can be modeled as a capacitive coupling to ground with a value approximately 1500 pF.

The middle electrode 416 of the three electrodes is driven by the control loop. When the middle electrode voltage is driven to the same amplitude and phase of the electrical excitation voltage (measured between Vp1 and Vcp), the current through the sensor resistive element may be driven to near zero dependent upon the control system methods.

Therefore, the control system according to embodiments includes current sensing element/node(s), a control point/node and a current verification node(s). The control system senses the leakage current via either a differential voltage across the leakage current sensor or via a non-contact current sensor and drives the control point to match the phase and amplitude of the first sensor node thus driving the leakage current to zero or near zero.

According to first embodiments, the disclosed subject matter includes a method that includes providing a first current sensor configured to detect electrical current flowing through a tube filled with a conductive fluid, providing a transducer configured to generate a current, providing a controller configured to receive as input a first signal from the first current sensor and to output a driving signal to the transducer, detecting the electrical current by the first current sensor and outputting the first signal from the first current sensor, receiving the first signal from the first current sensor by the controller, determining at least a magnitude of the detected electrical current, generating a driving signal based on the detected electrical current, and driving the transducer with the driving signal.

In variations thereof, the first embodiments include ones in which the method also includes providing a second current sensor and detecting the electrical current by the second current sensor and outputting a second signal from the second current sensor, wherein the controller is configured to generate the driving signal based at least on the first signal and the second signal.

In further variations thereof, the first embodiments include ones wherein the tube with the conductive fluid fluidly connects a patient to a medical device and is configured to convey the conductive fluid between the patient and the medical device, the first current sensor is positioned along the tube at a first position, the transducer is positioned along the tube at a second position, the second sensor is positioned along the tube at a third position, the first position is closest to the patient, the second position is between the first and second position, and the third position is farthest from the patient and closest to the medical device.

In further variations thereof, the first embodiments include ones wherein the medical device is a dialysis system.

In further variations thereof, the first embodiments include ones in which the tube is a blood line conveying blood between the patient and the medical device.

In further variations thereof, the first embodiments include ones in which the first sensor is clamped around the tube.

In further variations thereof, the first embodiments include ones in which the transducer is clamped around the tube.

In further variations thereof, the first embodiments include ones in which the second sensor is clamped around the tube.

In further variations thereof, the first embodiments include ones in which the providing the transducer includes clamping the transducer around the tube, the providing the first sensor includes clamping the first sensor around the tube, and the providing the second sensor includes clamping the second senor around the tube.

In further variations thereof, the first embodiments include ones in which the generating a driving signal includes setting a phase of the driving signal to match the phase of the detected electrical current, and setting a magnitude of the driving signal to be below the magnitude of the detected electrical current.

In further variations thereof, the first embodiments include ones in which a difference between the magnitude of the driving signal and the magnitude of the detected electrical current is a value based on an acceptable magnitude of a leakage current from the patient.

According to second embodiments, the disclosed subject matter includes a system for reducing the current flowing in a conductive fluid. The system may include a tube with a conductive fluid that electrically couples a patient with a medical device, wherein the conductive fluid comprises blood, a first current sensor clamped around the tube that measures a leakage current of the conductive fluid within the tube based on a magnetic field produced around the tube, wherein the first current sensor is located between the patient and a transducer, a second current sensor clamped around the tube that measures a leakage current of the conductive fluid within the tube based on a magnetic field produced around the tube, wherein the second current sensor is located between the transducer and the medical device, and a transducer clamped around the tube located between the first current sensor and the second current sensor, wherein a transducer controller controls the transducer to inject canceling current into the conductive fluid within the tube based on leakage current sensed by the first current sensor and the second current sensor, the canceling current reducing the leakage current of the conductive fluid to a threshold level.

In further variations thereof, the second embodiments include ones in which the patient is electrified with substantially 132 VAC rms and a leakage current for the conductive fluid is substantially 80 μA when the transducer is not injecting canceling current into the conductive fluid. 14. The system of claim 13, wherein canceling current is at least 75 μA.

In further variations thereof, the second embodiments include ones in which the leakage current of the conductive fluid comprises alternating current.

In further variations thereof, the second embodiments include ones in which the current sensed by the first current sensor and second current sensor is used by the transducer controller to adjust a phase of the injected canceling current to be in phase with the leakage current in the conductive fluid.

In further variations thereof, the second embodiments include ones in which the injected canceling current has phase shift from the leakage current in the conductive fluid.

In further variations thereof, the second embodiments include ones in which the phase shift is substantially 88 degrees.

In further variations thereof, the second embodiments include ones in which the canceling current is injected using magnetic field energy generated by the transducer and the transducer controller.

In further variations thereof, the second embodiments include ones in which the first current sensor, the second current sensor, and the transducer include open spaces and the tube is positioned within the open spaces.

In further variations thereof, the second embodiments include ones in which the threshold level comprises a threshold range between substantially 10 μA or 20 μA.

According to third embodiments, the disclosed subject matter includes a blood line for reducing electrical current during a medical treatment. The blood line includes a first segment of tubing having a first end fluidly connected to a patient access connector and an electrode coupled to a second end of the first segment of tubing, wherein the electrode comes into contact with blood that flows through the first segment during the medical treatment.

In further variations thereof, the third embodiments include ones in which the electrode has a circular cross-section and an outer diameter that is substantially the same as an inner diameter of the first segment of tubing, and the electrode is coupled to the second end of the first segment of tubing by insertion of the electrode into the second end.

In further variations thereof, the third embodiments include ones in which the electrode further includes a raised flange extending around an outer circumference of the electrode, and the flange rests against the second end of the first segment of tubing after the insertion of the electrode into the second end.

In further variations thereof, the third embodiments include ones in which the raised flange has a height measured from the outer diameter of the electrode greater than or equal to a thickness of a wall of the first segment of tubing.

In further variations thereof, the third embodiments include ones in which the raised flange has the height greater than the thickness of the wall of the first segment of tubing.

In further variations thereof, the third embodiments include ones in which the electrode has a tubular shape with a first opening and an opposed second opening, and at least the first opening tapers from a diameter that substantially matches the inner diameter of the first segment of tubing to a smaller diameter that matches a wall thickness of the electrode.

In further variations thereof, the third embodiments include ones in which the second opening tapers from a diameter that substantially matches the inner diameter of the first segment of tubing to the smaller diameter that matches the wall thickness of the electrode.

In further variations thereof, the third embodiments include ones in which the electrode has a circular cross-section and an inner diameter that is substantially the same as an outer diameter of the first segment of tubing, and the electrode is coupled to the second end of the first segment of tubing by insertion of the second end of the first segment of tubing into an end of the electrode.

In further variations thereof, the third embodiments include ones in which the electrode includes an internal rib that runs along an inner circumference of the electrode.

In further variations thereof, the third embodiments include ones in which the internal rib has an inner surface that comes into contact with blood flowing through the first segment of tubing during the medical treatment, the first segment of tubing abuts the internal rib on one side of the internal rib, a second segment of tubing abuts the internal rib on a second side of the internal rib, and the inner surface of the internal rib contacting the blood capacitively couples the electrode to the blood.

In further variations thereof, the third embodiments include ones in which the capacitive coupling has a capacitance value of at least 100 nF.

In further variations thereof, the third embodiments include ones in which the electrode has a resistance measured from an outer surface of the electrode to blood that is in contact with an internal surface of the electrode of less than 10,000 Ohms.

In further variations thereof, the third embodiments include ones in which the electrode is made of a conductor, such as steel, stainless steel, gold, gold alloy, titanium, or titanium alloy.

In further variations thereof, the third embodiments include ones in which the electrode is made at least partially out of a polymer.

In further variations thereof, the third embodiments include ones in which the polymer includes PVC.

In further variations thereof, the third embodiments include ones in which the electrode further includes a quantity of carbon suspended as a colloid in the polymer.

In further variations thereof, the third embodiments include ones in which the carbon makes up 15% to 35% of a total volume of the electrode.

In further variations thereof, the third embodiments include ones in which the electrode has a length measured along its principal axis of 1 inch.

According to fourth embodiments, the disclosed subject matter includes a blood line for reducing electrical current during a medical treatment. The blood line may include a first segment of tubing having a first end fluidly connected to a patient access connector, a first electrode coupled to a second end of the first segment of tubing, a second segment of tubing having a first end coupled to the first electrode, a second electrode coupled to a second end of the second segment of tubing, a third segment of tubing having a first end coupled to the second electrode, a third electrode coupled to a second end of the third segment of tubing, and a fourth segment of tubing having a first coupled to the third electrode. In further variations, the first electrode, the second electrode, and the third electrode come into contact with blood that flows through the segments of tubing during the medical treatment.

In further variations thereof, the fourth embodiments include ones in which the first electrode and the second electrode are separated by a first spacing, and the second electrode and the third electrode are separated by a second spacing.

In further variations thereof, the fourth embodiments include ones in which the first spacing and the second spacing are equal.

In further variations thereof, the fourth embodiments include ones in which each of the first, second, and third electrodes is made at least partially out of a polymer.

In further variations thereof, the fourth embodiments include ones in which the polymer includes PVC.

In further variations thereof, the fourth embodiments include ones in which the electrodes further include a quantity of carbon suspended as a colloid in the polymer.

In further variations thereof, the fourth embodiments include ones in which the carbon makes up 15% to 35% of a total volume of the electrode.

In further variations thereof, the fourth embodiments include ones in which a conductive region inside each electrode that comes into contact with blood forms a double layer capacitor with a capacitance greater than or equal to 100 nF.

In further variations thereof, the fourth embodiments include ones in which a medical device includes at least one blood line according to any of the variations of the fourth embodiments.

In further variations thereof, the fourth embodiments include ones in which the medical device also includes at least one contact clamp shaped and sized to accommodate the contact electrode and to create an electrical connection between the contact clamp and the electrode.

According to fifth embodiments, the disclosed subject matter includes a tracking generator, that may include a blood line according to any of the variations of the fourth embodiments, a sensor differential amplifier receiving an input from the first electrode and the second electrode, the senor differential amplifier outputting a signal representative of the difference in voltage between the second electrode and the first electrode. The tracking generator may also include a plurality of gain stages that amplify the output of the sensor differential amplifier, an electrical output of the gain stages applied to the second electrode to generate a current from the second electrode, through the third electrode, and to ground, and the third electrode disposed closest to the medical treatment machine.

In further variations thereof, the fifth embodiments include ones in which the sensor differential amplifier includes a transformer with a primary winding and a secondary winding, the first electrode is conductively connected to the one end of the primary winding, the second electrode is conductively connected to another end of the primary winding, and one end of the secondary winding is the output of the sensor differential amplifier and provided to the plurality of gain stages.

According to sixth embodiments, the disclosed subject matter includes a medical treatment system that is conductively coupled to a patient, for example by a blood line or a dialysate line. The medical treatment system accumulates waste fluid that may be conductive, and has a need to discharge the fluid to a drain. The medical treatment system includes a drain line 101 that has a conductive shield 129, that prevents or reduces capacitive coupling between fluid flowing through internal tube 125 and a conductor at ground potential (such as a metal floor on which the drain line 101 may be placed during use).

It is, thus, apparent that there is provided, in accordance with the present disclosure, systems, devices, and methods for reducing current flowing in a conductive fluid. Many alternatives, modifications, and variations are enabled by the present disclosure. Features of the disclosed embodiments and their variations can be combined, rearranged, omitted, etc., within the scope of the disclosure to produce additional embodiments and variations. Furthermore, certain features may sometimes be used to advantage without a corresponding use of other features. Accordingly, Applicants intend to embrace all such alternatives, modifications, equivalents, and variations that are within the spirit and scope of the present disclosure.

What is claimed is:

1. A method of reducing an electrical leakage current flowing through a tube filled with blood, the method comprising:

providing a first current sensor configured to detect the electrical leakage current flowing through the tube filled with the blood at a first location along said tube;

providing a second current sensor configured to detect the electrical leakage current flowing through the tube filled with the blood at a third location along said tube;

connecting a patient to a dialysis treatment system with said tube, the tube conveying the blood between the patient and the dialysis treatment system;

providing a transducer configured to generate an electrical current in the tube filled with the blood at a second location along said tube;

providing a controller configured to receive as input a first signal from the first current sensor and a second signal from the second current sensor and to output a driving signal to the transducer;

detecting the electrical leakage current by the first current sensor and outputting the first signal from the first current sensor to the controller;

detecting the electrical leakage current by the second current sensor and outputting the second signal from the second current sensor to the controller;

receiving the first signal from the first current sensor and the second signal from the second current sensor by the controller;

generating the driving signal by the controller based on at least both of the first signal from the first current sensor and the second signal from the second current sensor; and driving the transducer with the driving signal to thereby generate a canceling electrical current that reduces the electrical leakage current flowing through the tube filled with the blood between the patient and the dialysis treatment system, wherein the first location along said tube is closest to the patient, the second location along said tube is between the first location and third location, and the third location along said tube is farthest from the patient and closest to the dialysis treatment system.

2. The method according to claim 1, wherein the first current sensor is clamped around the tube.

3. The method according to claim 1, wherein the transducer is clamped around the tube.

4. The method according to claim 1, wherein the second current sensor is clamped around the tube.

5. The method according to claim 1, wherein the providing the transducer includes clamping the transducer around the tube, the providing the first current sensor includes clamping the first current sensor around the tube, and the providing the second current sensor includes clamping the second current sensor around the tube.

6. The method according to claim 5, wherein the generating the driving signal includes setting a phase of the driving signal to match the phase of the electrical leakage current detected by the first current sensor; and setting a magnitude of the driving signal to be below the magnitude of the detected electrical current.

7. The method according to claim 6, wherein the step of setting the magnitude of the driving signal includes determining a difference between the magnitude of the driving signal and the magnitude of the detected electrical current, and the magnitude of the driving signal is selected such that the difference is a value based on an acceptable magnitude of a leakage current from the patient.

8. A system for reducing electrical current flowing in a conductive fluid, the system comprising:

a tube with a conductive fluid that electrically couples a patient with a medical device, wherein the conductive fluid comprises blood;

a first current sensor clamped around the tube that measures a leakage current of the conductive fluid within the tube based on a magnetic field produced around the tube, wherein the first current sensor is located between the patient and a transducer;

a second current sensor clamped around the tube that measures a leakage current of the conductive fluid within the tube based on a magnetic field produced around the tube, wherein the second current sensor is located between the transducer and the medical device; and a transducer clamped around the tube located between the first current sensor and the second current sensor, wherein a transducer controller controls the transducer to inject canceling current into the conductive fluid within the tube based on leakage current sensed by the first current sensor and the second current sensor, the canceling current reducing the leakage current of the conductive fluid to a threshold level.

9. The system of claim 8, wherein the patient is electrified with a voltage level corresponding to a standard line voltage at a location of the system and the leakage current for the conductive fluid is substantially 80 μA when the transducer is not injecting canceling current into the conductive fluid.

10. The system of claim 9, wherein canceling current is at least 75 μA.

11. The system of claim 8, wherein the leakage current of the conductive fluid comprises alternating current.

12. The system of claim 11, wherein the current sensed by the first current sensor and the second current sensor is used by the transducer controller to adjust a phase of the canceling current injected by the transducer to be in phase with the leakage current in the conductive fluid.

13. The system of claim 12, wherein the canceling current has phase shift from the leakage current in the conductive fluid.

14. The system of claim 8, wherein the canceling current is injected using magnetic field energy generated by the transducer and the transducer controller.

15. The system of claim 8, wherein the first current sensor, the second current sensor, and the transducer comprise open spaces and the tube is positioned within the open spaces.

16. The system of claim 8, wherein the threshold level comprises a threshold range between 10 μA and 20 μA.

* * * * *